(12) United States Patent
Komatsu et al.

(10) Patent No.: US 8,212,053 B2
(45) Date of Patent: Jul. 3, 2012

(54) PROCESS FOR PREPARING HETEROAROMATIC RING COMPOUND HAVING N-RF GROUP

(75) Inventors: Yuzo Komatsu, Settsu (JP); Haruhiko Mohri, Settsu (JP); Hirokazu Aoyama, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 661 days.

(21) Appl. No.: 12/159,439

(22) PCT Filed: Dec. 11, 2006

(86) PCT No.: PCT/JP2006/324671
§ 371 (c)(1),
(2), (4) Date: Jun. 27, 2008

(87) PCT Pub. No.: WO2007/074632
PCT Pub. Date: Jul. 5, 2007

(65) Prior Publication Data
US 2010/0222598 A1  Sep. 2, 2010

(30) Foreign Application Priority Data
Dec. 28, 2005  (JP) ................. 2005-379619

(51) Int. Cl.
*C07D 233/54* (2006.01)
*C07D 233/60* (2006.01)
(52) U.S. Cl. .................. 548/341.1
(58) Field of Classification Search ........... 548/341.1
See application file for complete search history.

(56) References Cited

U.S. PATENT DOCUMENTS

| | | | |
|---|---|---|---|
| 2,861,990 A | 11/1958 | Cleaver et al. | |
| 4,657,921 A | 4/1987 | Frick et al. | |
| 4,690,942 A | 9/1987 | Frick et al. | |

FOREIGN PATENT DOCUMENTS

| | | |
|---|---|---|
| EP | 0 163 606 A2 | 12/1985 |
| EP | 0 248 765 A2 | 12/1987 |
| JP | 60-222464 A | 11/1985 |
| JP | 60-258167 A | 12/1985 |
| JP | 62-292760 A | 12/1987 |
| JP | 2007-112722 A | 5/2007 |
| WO | WO 2005072376 A2 | 8/2005 |
| WO | WO 2005085181 A1 | 9/2005 |

OTHER PUBLICATIONS

Bissky et al., Synlett, 2001, No. 3, 374-378.*
Walter Ried, et al., "Die Addition von Trifluorchlorathylen an Imidazol, Benzimidazol, und Naphthimidazol. Eine neue Spaltung des Imidazolringes," Justus Liebigs Annalen der Chemie, 1966, p. 88-97, vol. 699.
Ki-Whan Chi, et al., "A Facile Synthesis of Partly-fluorinated Organic Compounds Using Perfluoropropoxyethylene and Amines," Bulletin of the Korean Chemical Society, 1999, p. 499-502, vol. 20, No. 5.
Vitalij V. Rudyuk, et al., "N-Polyfluoroethyl and N-2-chlorodifluorovinyl derivatives of azoles," Journal of Fluorine Chemistry, 2004, p. 1465-1471, vol. 125, No. 10.
Yurii L. Yagupolskii, et al.; "Novel ionic liquids—Imidazolium salts with a difluoromethylene fragment directed bonded to the nitrogen atom"; Journal of Fluorine Chemistry; vol. 126, No. 4; Apr. 19, 2005; pp. 669-672; XP-002642008.
Database Caplus; Xiao, Ji-Chang et al.; "Reaction of imidazole anions with difluorodiiodomethane and their products conversion in sulfinatodehalogenation system"; XP-002642009, 2003.
Database Caplus; Chi, Ki-Whan et al; "A facile synthesis of partly fluorinated organic compounds using perfluoro(propoxyethylene) and amines"; XP-002642010, 1999.
German Bissky, et al.; "Heteroaryl-N-difluoromethyltrimethylsilanes—Versatile Sources of Heteroaryl-N-difluoromethyl Anions in Reactions with Carbonyl Compounds"; Synlett; No. 3; 2001; pp. 374-378; XP-002642011.
Database Caplus; Poludnenko, V.G. et al; "Fluorine-containing azoles. 3. Reaction of imidazoles and perimidines with perfluoroalkenes" ; XP-002642012, 1984.

* cited by examiner

*Primary Examiner* — Rebecca Anderson
(74) *Attorney, Agent, or Firm* — Sughrue Mion, PLLC

(57) ABSTRACT

There is provided a preparation process in which a N—H group of a heteroaromatic ring compound having a N—H group in its ring is converted directly to a N—Rf group at a high reaction efficiency without using a catalyst. The preparation process is a process for preparing a compound comprising a heteroaromatic ring structure having a N—Rf group (—Rf is a fluorine-containing organic group) in its ring and is characterized in that the heteroaromatic ring compound having a N—H group in its ring is allowed to react with fluoroalkene in the absence of an alkali metal.

2 Claims, No Drawings

PROCESS FOR PREPARING HETEROAROMATIC RING COMPOUND HAVING N-RF GROUP

TECHNICAL FIELD

The present invention relates to a process for preparing a heteroaromatic ring compound which is useful as a starting material for a salt of heteroaromatic ring compound usable as an ionic liquid, a curing agent such as an epoxy resin or a polyurethane resin, various agricultural chemicals, intermediates for medicines such as antibiotics and anti-AIDS drugs and intermediates of dye, and further relates to a process for preparing a salt of heteroaromatic ring compound.

BACKGROUND ART

Liquid salts of imidazole compounds have ionic conductivity, flame retardance, non-volatility, high polarity and solubility, and by making use of these properties, are expected to be ionic liquids having various functions useful for electrolytes for fuel cell, secondary battery, capacitor, dye-sensitized solar cell and electrochromic device, or reaction media, catalyst, and chemical separation and reprocessing of nuclear fuel.

For example, JP2003-62467A discloses an ionic liquid composition containing 1-(2,2,2-trifluoroethyl)-3-methylimidazolium trifluoromethanesulfonate. This salt of an imidazole compound is prepared by allowing 1-(methoxyethyl)-3-methylimidazolium trifluoromethanesulfonate to react with trifluoromethanesulfonic anhydride in the presence of trifluoroethanol and pyridine as disclosed in P. Bonhote et al., Inorganic Chemistry, 35, pp. 1168-1178 (1996). However in this preparation process, separation of impurities derived from unreacted imidazolium salt is difficult, and in addition, an expensive reacting agent is used and yield is as low as about 28%. Also in the structure of this imidazolium salt, a fluorine-containing alkyl group is not introduced directly on nitrogen, and an effect of increasing cations for use as a Lewis acid catalyst is difficult to obtain.

V. V. Rudyuk et al., J. Fluorine Chem., 125, pp. 1465-1471 (2004) discloses that after conversion of an imidazole compound into a potassium salt, when the potassium salt is allowed to react with $CF_2$=CFCl under refluxing in dimethylacetamide, an imidazole compound in which N—K groups of the imidazole compound have been converted to N—CF=CFCl groups and N—$CF_2$CFCl groups can be obtained, and yield of the imidazole compound having N—$CF_2$CFCl groups is 20 to 85%, and also discloses that when an imidazole compound is allowed to react directly with $CF_2$=$CF_2$ in tetrahydrofuran in the presence of a catalytic amount of metallic potassium, an imidazole compound in which N—H groups of the imidazole compound have been converted to N—$CF_2$CFH groups can be obtained at yield of 68%.

D. C. England et al., J. Am. Chem. Soc., 82, pp. 5116-5122 (1960) and U.S. Pat. No. 2,861,990 disclose that a pyrrole compound or an indole compound is allowed to react with fluoroalkene such as $CF_2$=$CF_2$, $CF_2$=CFCl or $CF_2$=$CFCF_3$ in the presence of metallic potassium or metallic sodium, and a pyrrole compound or an indole compound in which a N—H group of the pyrrole compound or the indole compound has been added to the fluoroalkene can be obtained at yield of 60 to 88%.

Alkali metals described in these V. V. Rudyuk et al., J. Fluorine Chem., 125, pp. 1465-1471 (2004), D. C. England et al., J. Am. Chem. Soc., 82, pp. 5116-5122 (1960) and U.S. Pat. No. 2,861,990 are substances which are so easily reactable with water, and handling thereof is not easy because water control of all chemicals to be used in the reaction and water control in working environment are necessary. In addition, in these processes, a step for removing alkali metal salt produced after the reaction is required.

Further, for ionization of an obtained imidazole compound having a fluoroalkyl group, there is employed a method of anion exchange by substitution reaction of the compound with methyl iodide as disclosed in Y. L. Yagupolskii et al., J. Fluorine Chem., 126, pp. 669-672 (2005).

DISCLOSURE OF INVENTION

The present inventors have studied a process for preparing an imidazole compound having a fluorine-containing group at high yield, and as a result, unexpectedly have found that by subjecting an imidazole compound in a molten state to reaction in the absence of a solvent, an imidazole compound having a fluorine-containing group can be prepared at high yield even without forming the imidazole compound into an alkali metal salt or using a catalytic amount of alkali metal. The present inventors have made further investigations based on this finding, and have completed the present invention.

Namely, the present invention relates to a process (the first preparation process) for preparing a compound (C) comprising a heteroaromatic ring structure having a N—Rf group in its ring, which is characterized in that a heteroaromatic ring compound (A) having a N—H group in its ring is allowed to react, in the absence of alkali metal, with a fluoroalkene (B) represented by the formula (B):

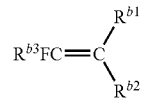

wherein $R^{b1}$, $R^{b2}$ and $R^{b3}$ are the same or different and each is H, halogen atom, a functional group or a monovalent organic group which may be substituted by halogen atom, may have an ether bond and may have a polymerizable group, and —Rf is represented by the formula (c):

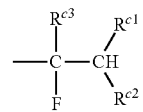

wherein $R^{c1}$ is the same as $R^{b1}$ of the formula (B); $R^{c2}$ is the same as $R^{b2}$ of the formula (B); $R^{c3}$ is the same as $R^{b3}$ of the formula (B).

Also the present invention relates to a process (the second preparation process) for preparing a salt (E) comprising a heteroaromatic ring structure having a N—Rf group in its ring, which is characterized in that subsequently to the above-mentioned preparation process, a salt forming compound (D) is acted on the obtained compound (C) comprising a heteroaromatic ring structure having a N—Rf group in its ring and if necessary, anion exchanging is further carried out.

The present invention further relates to a novel compound (C1) comprising a heteroaromatic ring structure having a N—Rf group in its ring and a novel salt (E1) comprising a heteroaromatic ring structure having a N—Rf group in its ring.

BEST MODE FOR CARRYING OUT THE INVENTION

The first preparation process of the present invention is a process for preparing the compound (C) comprising a heteroaromatic ring structure having a N—Rf group in its ring, which is characterized in that the heteroaromatic ring compound (A) having a N—H group in its ring is allowed to react, in the absence of alkali metal, with the fluoroalkene (B) represented by the above-mentioned formula (B).

Examples of the heteroaromatic ring compound (A) having a N—H group in its ring which is a starting material are heteroaromatic ring compounds (A1) represented by the formula (A1):

wherein

is a moiety forming a heteroaromatic ring together with a nitrogen atom and the whole or a part of its hydrogen atoms may be substituted by the same or different organic groups.

Among such compounds, a compound having an imidazole skeleton, a pyrrole skeleton, a pyrazole skeleton, a triazole skeleton, an indole skeleton, a purine skeleton or a purine derivative is preferable from the viewpoint of easy synthesis and availability.

Especially examples of the heteroaromatic ring compound (A1) represented by the above-mentioned formula (A1) are an imidazole compound represented by the formula (A1-1):

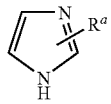

wherein $R^a$s are the same or different, and each is halogen atom, a functional group or an organic group and may be present or may not be present, and when $R^a$s are present, the whole or a part of hydrogen atoms of the heteroaromatic ring are substituted by them, a pyrrole compound represented by the formula (A1-2):

wherein $R^a$s are the same or different, and each is halogen atom, a functional group or an organic group and may be present or may not be present, and when $R^a$s are present, the whole or a part of hydrogen atoms of the heteroaromatic ring are substituted by them, a pyrazole compound represented by the formula (A1-3):

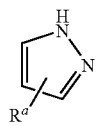

wherein $R^a$s are the same or different, and each is halogen atom, a functional group or an organic group and may be present or may not be present, and when $R^a$s are present, the whole or a part of hydrogen atoms of the heteroaromatic ring are substituted by them, a triazole compound represented by the formula (A1-4):

wherein $R^a$s are the same or different, and each is halogen atom, a functional group or an organic group and may be present or may not be present, and when $R^a$s are present, the whole or a part of hydrogen atoms of the heteroaromatic ring are substituted by them, an indole compound represented by the formula (A1-5):

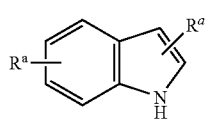

wherein $R^a$s are the same or different, and each is halogen atom, a functional group or an organic group and may be present or may not be present, and when $R^a$s are present, the whole or a part of hydrogen atoms of the heteroaromatic ring and/or the aromatic ring are substituted by them, a purine compound represented by the formula (A1-6):

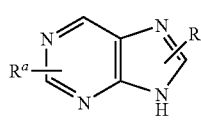

wherein $R^a$s are the same or different, and each is halogen atom, a functional group or an organic group and may be present or may not be present, and when $R^a$s are present, the whole or a part of hydrogen atoms of the heteroaromatic ring and/or the aromatic ring are substituted by them, and a purine derivative represented by the formula (A1-7):

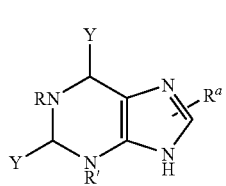

wherein $R^a$ is halogen atom, a functional group or an organic group and may be present or may not be present, and when $R^a$ is present, the whole or a part of hydrogen atoms of the heteroaromatic ring are substituted by $R^a$; R and R' are the same or different and each is hydrogen atom, an alkyl group, an arylalkyl group, an organosilicon group, an alkoxyl group or a carboxyester group; Ys are the same or different and each is =O, —NRR', —OR, F or $F_2$, and compounds explained infra.

Examples of $R^a$ are, for instance, groups raised below.

(a1-1) Halogen Atoms:

There are preferably fluorine atom and chlorine atom, especially fluorine atom.

(a1-2) Functional Groups:

Examples are carboxyl group (—COOH), carboxylic acid ester group (—COOR), nitrile group (—CN), amino group (—$NH_2$), alkylamino group (—$NR_2$, —NHR), carboxamide group (—$CONR_2$, —CONHR), alkyl ether group (—OR), silyl ether group (—$OSiR_3$), thiol group (—SH), thioether group (—SR) and nitro group, preferably carboxylic acid ester group, nitrile group, amino group, alkylamino group, carboxamide group, alkyl ether group, silyl ether group, thiol group and thioether group. In addition, carboxyl group (—COOH), carboxylic acid ester group (—COOR), nitrile group (—CN), amino group (—$NH_2$), alkylamino group (—$NR_2$, —NHR), carboxamide group (—$CONR_2$, —CONHR), alkyl ether group (—OR), silyl ether group (—$OSiR_3$), thiol group (—SH), thioether group (—SR) and nitro group are allowable as a substituent group to be bonded to the benzene ring (Rs are the same or different, and are preferably monovalent hydrocarbon groups).

(a1-3) Organic Groups:

(a1-3-1) Linear or branched alkyl groups in which a part or the whole of hydrogen atoms may be substituted by halogen atoms, preferably fluorine atoms. The number of carbon atoms is preferably 1 to 1,000.

(a1-3-2) Alkyl groups substituted by functional group such as carboxyl group, hydroxyl group, nitrile group, amino group, alkylamino group, carboxylic acid ester group, carboxamide group, alkyl ether group, silyl ether group, thiol group, thioether group or nitro group. The number of carbon atoms is preferably 1 to 20.

(a1-3-3) Aryl groups which may be substituted.

(a1-3-4) Alkyl groups having ether bond in which a part or the whole of hydrogen atoms may be substituted by halogen atoms, preferably fluorine atoms. The number of carbon atoms is preferably 1 to 1,000.

(a1-3-5) Alkoxyl groups in which a part or the whole of hydrogen atoms may be substituted by halogen atoms, preferably fluorine atoms. The number of carbon atoms is preferably 1 to 1,000.

In the following Tables 1 to 13, definitions of substituents are effective only in the corresponding tables. Figures showing the number of atoms are not represented especially by small letters. Further Ph, i and n are abbreviations of phenyl, iso and normal, respectively.

Examples of the imidazole compounds of the formula (A1-1) are, for instance, compounds having $R^{a1}$ shown in Table 1.

TABLE 1

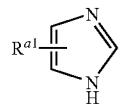

Imidazole

| Compound No. | $R^{a1}$ | | |
|---|---|---|---|
| A1-1-1 | H | H | H |
| 2 | F | H | H |
| 3 | F | F | H |
| 4 | F | F | F |
| 5 | CF3 | H | H |
| 6 | CF3 | F | H |
| 7 | C2F5 | H | H |
| 8 | iC3F7 | H | H |
| 9 | C4H9 | H | H |
| 10 | CHF2CF2 | H | H |
| 11 | CF3CHFCF2 | H | H |
| 12 | CH3 | H | H |
| 13 | CH3 | F | H |
| 14 | CH3 | CH3 | H |
| 15 | Ph | H | H |
| 16 | Ph | F | H |
| 17 | CH3 | Ph | H |
| 18 | C2H5 | H | H |
| 19 | nC3H7 | H | H |
| 20 | iC3H7 | H | H |
| 21 | nC4H9 | H | H |
| 22 | CH2OR | H | H |
| 23 | COOR | H | H |
| 24 | COOR | F | H |
| 25 | Cl | H | H |
| 26 | C4H9 | CH2OR | Cl |
| 27 | CH2CH(NRR')COOR | H | H |
| 28 | CH2CH(NRR')COOR | F | H |
| 29 | CH2CN | H | H |
| 30 | CH2CN | F | H |
| 31 | CH2COOH | H | H |
| 32 | CH2COOH | F | H |

Examples of the pyrrole compounds of the formula (A1-2) are, for instance, compounds having $R^{a2}$ shown in Table 2.

TABLE 2

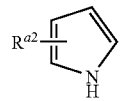

Pyrrole

| Compound No. | $R^{a2}$ | | | |
|---|---|---|---|---|
| A1-2-1 | H | H | H | H |
| 2 | F | H | H | H |
| 3 | F | F | H | H |
| 4 | F | F | F | H |
| 5 | F | F | F | F |
| 6 | CF3 | H | H | H |
| 7 | CF3 | F | H | H |
| 8 | CF3 | F | F | H |
| 9 | C2F5 | H | H | H |
| 10 | iC3F7 | H | H | H |
| 11 | C4F9 | H | H | H |
| 12 | CH3 | H | H | H |
| 13 | CH3 | F | H | H |
| 14 | CH3 | CH3 | H | H |
| 15 | Ph | H | H | H |
| 16 | Ph | F | H | H |
| 17 | CH3 | Ph | H | H |
| 18 | C2H5 | H | H | H |
| 19 | nC3H7 | H | H | H |

TABLE 2-continued

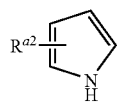

Pyrrole

| Compound No. | $R^{a2}$ | | | |
|---|---|---|---|---|
| 20 | iC3H7 | H | H | H |
| 21 | nC4H9 | H | H | H |
| 22 | CH2OR | H | H | H |
| 23 | COOR | H | H | H |
| 24 | COOR | F | H | H |
| 25 | Cl | H | H | H |
| 26 | CH(NRR')COOR | H | H | H |
| 27 | CH(NRR')COOR | F | H | H |
| 28 | CH2CH2NRR' | H | H | H |
| 29 | CH2CH2NRR' | F | H | H |
| 30 | CH2CN | H | H | H |
| 31 | CH2CN | F | H | H |
| 32 | CH2COOH | H | H | H |
| 33 | CH2COOH | F | H | H |

Examples of the pyrazole compounds of the formula (A 1-3) are, for instance, compounds having $R^{a3}$ shown in Table 3.

TABLE 3

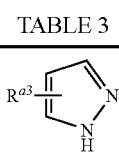

Pyrazole

| Compound No. | $R^{a3}$ | | | |
|---|---|---|---|---|
| A1-3-1 | H | H | H | |
| 2 | F | H | H | |
| 3 | F | F | H | |
| 4 | F | F | F | |
| 5 | CF3 | H | H | |
| 6 | CF3 | F | H | |
| 7 | C2F5 | H | H | |
| 8 | iC3F7 | H | H | |
| 9 | C4F9 | H | H | |
| 10 | CHF2CF2 | H | H | |
| 11 | CF3CHFCF2 | H | H | |
| 12 | CH3 | H | H | |
| 13 | CH3 | F | H | |
| 14 | CH3 | CH3 | H | |
| 15 | Ph | H | H | |
| 16 | Ph | F | H | |
| 17 | CH3 | Ph | H | |
| 18 | C2H5 | H | H | |
| 19 | nC3H7 | H | H | |
| 20 | iC3H7 | H | H | |
| 21 | nC4H9 | H | H | |
| 22 | CH2OR | H | H | |
| 23 | COOR | H | H | |
| 24 | COOR | F | H | |
| 25 | Cl | H | H | |

Examples of the triazole compounds of the formula (A1-4) are, for instance, 1,2,4-triazole compounds having $R^{a4}$ shown in Table 4.

TABLE 4

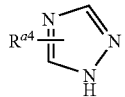

Triazole

| Compound No. | $R^{a4}$ | |
|---|---|---|
| A1-4-1 | H | H |
| 2 | F | H |
| 3 | F | F |
| 4 | CF3 | H |
| 5 | CF3 | F |
| 6 | C2F5 | H |
| 7 | iC3F7 | H |
| 8 | C4F9 | H |
| 9 | CHF2CF2 | H |
| 10 | CF3CHFCF2 | H |
| 11 | CH3 | H |
| 12 | CH3 | F |
| 13 | CH3 | CH3 |
| 14 | Ph | H |
| 15 | Ph | F |
| 16 | CH3 | Ph |
| 17 | C2H5 | H |
| 18 | nC3H7 | H |
| 19 | iC3H7 | H |
| 20 | nC4H9 | H |
| 21 | CH2OR | H |
| 22 | COOR | H |
| 23 | COOR | F |
| 24 | Cl | H |
| 25 | Cl | F |

Examples of the indole compounds of the formula (A1-5) are, for instance, compounds having $R^{a5}$ and $R^{a6}$ shown in Table 5.

TABLE 5

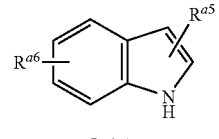

Indole

| Compound No. | $R^{a6}$ | | | | $R^{a5}$ | |
|---|---|---|---|---|---|---|
| A1-5-1 | H | H | H | H | H | H |
| 2 | F | H | H | H | H | H |
| 3 | F | F | H | H | H | H |
| 4 | H | H | H | H | F | H |
| 5 | F | H | H | H | F | H |
| 6 | H | H | H | H | CH3 | H |
| 7 | F | H | H | H | CH3 | H |
| 8 | COOR | H | H | H | H | H |
| 9 | COOR | F | H | H | H | H |
| 10 | H | H | H | H | COOR | H |
| 11 | F | H | H | H | COOR | H |
| 12 | H | H | H | H | CH(NRR')COOR | H |
| 13 | F | H | H | H | CH(NRR')COOR | H |
| 14 | H | H | H | H | CH2NRR' | H |
| 15 | F | H | H | H | CH2NRR' | H |
| 16 | H | H | H | H | CN | H |
| 17 | F | H | H | H | CN | H |

Examples of the purine compounds of the formula (A1-6) are, for instance, compounds having $R^{a7}$ and $R^{a8}$ shown in Table 6.

TABLE 6

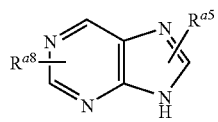

Purine

| Compound No. | $R^{a8}$ | | $R^{a7}$ |
|---|---|---|---|
| A1-6-1 | H | H | H |
| 2 | F | H | H |
| 3 | F | F | H |
| 4 | H | H | F |
| 5 | F | H | F |
| 6 | H | H | CF3 |
| 7 | F | H | CF3 |
| 8 | H | H | CH3 |
| 9 | F | H | CH3 |
| 10 | COOR | H | H |
| 11 | COOR | F | H |
| 12 | CH3 | H | H |
| 13 | CH3 | F | H |
| 14 | Ph | H | H |
| 15 | Ph | F | H |
| 16 | CH3 | H | H |
| 17 | CH3 | F | H |
| 18 | NR2 | H | H |
| 19 | NR2 | F | H |
| 20 | OR | H | H |
| 21 | OR | F | H |

Examples of the purine derivatives of the formula (A1-7) are, for instance, compounds having $R^{a9}$ shown in Table 7.

TABLE 7

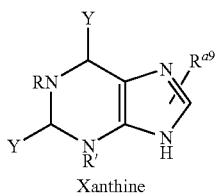

Xanthine

| Compound No. | Y | | $R^{a9}$ |
|---|---|---|---|
| A1-7-1 | =O | =O | H |
| 2 | =O | =O | CH3 |
| 3 | =O | =O | Ph |
| 4 | =O | =O | OR |
| 5 | =O | =O | F |
| 6 | =O | NRR' | H |
| 7 | =O | NRR' | CH3 |
| 8 | =O | OR | H |
| 9 | =O | OR | CH3 |
| 10 | =O | F | H |
| 11 | =O | F | CH3 |
| 12 | =O | F2 | H |
| 13 | =O | F2 | CH3 |
| 14 | =O | F2 | Ph |
| 15 | =O | F2 | OR |
| 16 | =O | F2 | F |

R or R' = H, CH3, Si(CH3)3, Si(CH3)2tBu, Si(iPr)3, SiEt3, CH2Ph, C(Ph)3, CH3CO, COOMe, COOtBu

Examples of other heteroaromatic ring compounds (A) are, for instance, benzimidazole compounds shown in Table 8, 1,2,3-triazole compounds shown in Table 9, tetrazole compounds shown in Table 10, isoindole compounds shown in Table 11, indazole compounds shown in Table 12 and benzotriazole compounds shown in Table 13.

TABLE 8

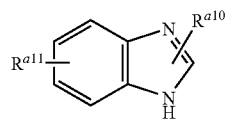

Benzimidazole

| Compound No. | $R^{a11}$ | | | | $R^{a10}$ |
|---|---|---|---|---|---|
| A1-8-1 | H | H | H | H | H |
| 2 | F | H | H | H | H |
| 3 | F | F | H | H | H |
| 4 | H | H | H | H | F |
| 5 | F | H | H | H | F |
| 6 | H | H | H | H | CF3 |
| 7 | F | H | H | H | CF3 |
| 8 | H | H | H | H | CH3 |
| 9 | F | H | H | H | CH3 |
| 10 | F | F | H | H | CH3 |
| 11 | COOR | H | H | H | H |
| 12 | COOR | F | H | H | H |
| 13 | CH3 | H | H | H | H |
| 14 | CH3 | F | H | H | H |
| 15 | Ph | H | H | H | H |
| 16 | Ph | F | H | H | H |
| 17 | CH3 | H | H | H | H |
| 18 | CH3 | F | H | H | H |
| 19 | H | H | H | H | COOR |
| 20 | F | H | H | H | COOR |
| 21 | F | F | H | H | COOR |
| 22 | H | H | H | H | CN |
| 23 | F | H | H | H | CN |
| 24 | F | F | H | H | CN |

TABLE 9

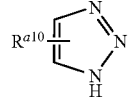

Triazole

| Compound No. | $R^{a10}$ | |
|---|---|---|
| A1-9-1 | H | H |
| 2 | F | H |
| 3 | F | F |
| 4 | CF3 | H |
| 5 | CF3 | F |
| 6 | C2F5 | H |
| 7 | iC3F7 | H |
| 8 | C4F9 | H |
| 9 | CHF2CF2 | H |
| 10 | CF3CHFCF2 | H |
| 11 | CH3 | H |
| 12 | CH3 | F |
| 13 | CH3 | CH3 |
| 14 | Ph | H |
| 15 | Ph | F |
| 16 | CH3 | Ph |
| 17 | C2H5 | H |
| 18 | nC3H7 | H |
| 19 | iC3H7 | H |
| 20 | nC4H9 | H |
| 21 | CH2OR | H |
| 22 | COOR | H |
| 23 | COOR | F |
| 24 | Cl | H |
| 25 | Cl | F |

TABLE 10

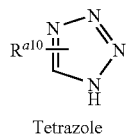

Tetrazole

| Compound No. | $R^{a10}$ |
|---|---|
| A1-10-1 | H |
| 2 | F |
| 3 | CF3 |
| 4 | C2F5 |
| 5 | iC3F7 |
| 6 | C4F9 |
| 7 | CHF2CF2 |
| 8 | CF3CHFCF2 |
| 9 | CH3 |
| 10 | Ph |
| 11 | C2H5 |
| 12 | nC3H7 |
| 13 | iC3H7 |
| 14 | nC4H9 |
| 15 | CH2OR |
| 16 | COOR |
| 17 | Cl |

TABLE 11

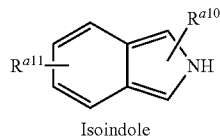

Isoindole

| Compound No. | $R^{a11}$ | | | | $R^{a10}$ | |
|---|---|---|---|---|---|---|
| A1-11-1 | H | H | H | H | H | H |
| 2 | F | H | H | H | H | H |
| 3 | F | F | H | H | H | H |
| 4 | H | H | H | H | F | H |
| 5 | F | H | H | H | F | H |
| 6 | H | H | H | H | CH3 | H |
| 7 | F | H | H | H | CH3 | H |
| 8 | COOR | H | H | H | H | H |
| 9 | COOR | F | H | H | H | H |
| 10 | H | H | H | H | COOR | H |
| 11 | F | H | H | H | COOR | H |
| 12 | H | H | H | H | CH(NRR')COOR | H |
| 13 | F | H | H | H | CH(NRR')COOR | H |
| 14 | H | H | H | H | CH2NRR' | H |
| 15 | F | H | H | H | CH2NRR' | H |
| 16 | H | H | H | H | CN | H |
| 17 | F | H | H | H | CN | H |

TABLE 12

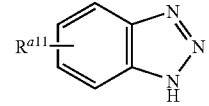

Indazole

| Compound No. | $R^{a11}$ | | | | $R^{a10}$ |
|---|---|---|---|---|---|
| A1-12-1 | H | H | H | H | H |
| 2 | F | H | H | H | H |
| 3 | F | F | H | H | H |
| 4 | H | H | H | H | F |

TABLE 12-continued

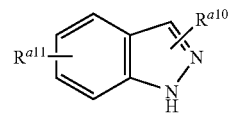

Indazole

| Compound No. | $R^{a11}$ | | | | $R^{a10}$ |
|---|---|---|---|---|---|
| 5 | F | H | H | H | F |
| 6 | H | H | H | H | CF3 |
| 7 | F | H | H | H | CF3 |
| 8 | H | H | H | H | CH3 |
| 9 | F | H | H | H | CH3 |
| 10 | F | F | H | H | CH3 |
| 11 | COOR | H | H | H | H |
| 12 | COOR | F | H | H | H |
| 13 | CH3 | H | H | H | H |
| 14 | CH3 | F | H | H | H |
| 15 | Ph | H | H | H | H |
| 16 | Ph | F | H | H | H |
| 17 | CH3 | H | H | H | H |
| 18 | CH3 | F | H | H | H |
| 19 | H | H | H | H | COOR |
| 20 | F | H | H | H | COOR |
| 21 | F | F | H | H | COOR |
| 22 | H | H | H | H | CN |
| 23 | F | H | H | H | CN |
| 24 | F | F | H | H | CN |

TABLE 13

Benzotriazole

| Compound No. | $R^{a11}$ | | | |
|---|---|---|---|---|
| A1-13-1 | H | H | H | H |
| 2 | F | H | H | H |
| 3 | F | F | H | H |
| 4 | F | F | F | H |
| 5 | F | F | F | F |
| 6 | COOR | H | H | H |
| 7 | COOR | F | H | H |
| 8 | CH3 | H | H | H |
| 9 | CH3 | F | H | H |
| 10 | Ph | H | H | H |
| 11 | Ph | F | H | H |
| 12 | OR | H | H | H |
| 13 | OR | F | H | H |

The fluoroalkene (B) which is allowed to react with the heteroaromatic ring compound (A) and is represented by the formula (B):

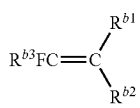

wherein $R^{b1}$, $R^{b2}$ and $R^{b3}$ are the same or different and each is H, halogen atom, a functional group or a monovalent organic group which may be substituted by halogen atom, may have an ether bond and may have a polymerizable group, is one being capable of undergoing addition reaction with the N—H group of the heteroaromatic ring compound (A).

It is preferable that at least one of $R^{b1}$, $R^{b2}$ and $R^{b3}$, especially at least either $R^{b1}$ or $R^{b2}$ has the formula (b-1):

$$—(CF_2)_{m1}—$$

wherein m1 is an integer of 1 to 10,000,
the formula (b-2):

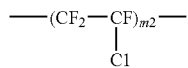

wherein m2 is an integer of 1 to 10,000,
the formula (b-3):

$$—(CF_2—CH_2)_{m3}—$$

wherein m3 is an integer of 1 to 10,000,
the formula (b-4):

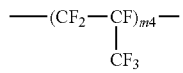

wherein m4 is an integer of 1 to 3,000, and/or
the formula (b-5):

$$—(Rf^bO)_{m5}—$$

wherein $Rf^b$ is a linear or branched alkylene group having fluorine atom; m5 is an integer of 1 to 100. Especially preferable is one having the perfluoroalkylene group of the formula (b-4) having a branched chain and/or the fluoroether unit of the formula (b-5) since a liquid state is easily exhibited at room temperature.

In addition, the end of at least one of $R^{b1}$, $R^{b2}$ and $R^{b3}$ may be a polymerizable group (b-6). Examples of the polymerizable group are, for instance, a carbon-carbon double bond, a hydroxyl group, a carboxyl group, an amino group, an isocyanate group, a thiol group and a thioisocyanate group, especially preferably a carbon-carbon double bond.

From a different point of view, preferable examples of $R^{b1}$, $R^{b2}$ and $R^{b3}$ are those raised below.
(b1-1) Hydrogen Atom
(b1-2) Halogen Atoms:
  There are chlorine atom, fluorine atom, and bromine atom, and fluorine atom is especially preferable.
(b1-3) Functional Groups:
  There are preferably a carboxyl group (—COOH), a carboxylic acid ester group (—COOR), a nitrile group (—CN) and an amino group.
(b1-4) Organic Groups:
(b1-4-1) Linear or branched alkyl groups, in which a part or the whole of hydrogen atoms may be substituted by halogen atoms, preferably fluorine atoms.
(b1-4-2) Alkyl groups having functional group such as carboxyl group, hydroxyl group, nitrile group or amino group.
(b1-4-3) Aryl groups which may be substituted.
(b1-4-4) Alkyl groups having an ether bond, in which a part or the whole of hydrogen atoms may be substituted by halogen atoms, preferably fluorine atoms.
(b1-4-5) Alkoxyl groups, in which a part or the whole of hydrogen atoms may be substituted by halogen atoms, preferably fluorine atoms.

Preferable examples of the fluoroalkene (B) are, for instance, fluorine-containing olefins such as $CF_2=CF_2$, $CF_2=CF(CF_3)$, $CF_2=C(CF_3)_2$, $CF_2=C(CF_3)Br$, $CF_2=C(CF_3)Cl$, $CF_2=C(CF_3)I$, $CF_2=CFBr$, $CF_2=CFCl$, $CF_2=CFI$, $(CF_3)_2CFCF_2CF=CF_2$, $(CF_3)_2CFCF=CFCF_3$, $(CF_3)_2C=CFCF_2CF_3$, $CF_2=CH_2$, $CF_2=CFH$, $CF_2=CF(Rf^B)_nCF=CH_2$ ($Rf^B$ is $CF_2CF_2$, $CF_2CFCl$, $CF_2CF(CF_3)$ or $CF_2CH_2$; n is 0 or an integer of 1 to 1,000), $CF_2=CF(Rf^B)_n—CF=CF_2$ ($Rf^B$ is $CF_2CF_2$, $CF_2CFCl$, $CF_2CF(CF_3)$ or $CF_2CH_2$; n is 0 or an integer of 1 to 1,000), $CF_2=CH(Rf^B)_n—CH=CF_2$ ($Rf^B$ is $CF_2CF_2$, $CF_2CFCl$, $CF_2CF(CF_3)$ or $CF_2CH_2$; n is 0 or an integer of 1 to 1,000), $CF_2=CH(Rf^B)_n—CF=CF_2$ ($Rf^B$ is $CF_2CF_2$, $CF_2CFCl$, $CF_2CF(CF_3)$ or $CF_2CH_2$; n is 0 or an integer of 1 to 1,000), $CF_2=CF(Rf^B)_n—F$ ($Rf^B$ is $CF_2CF_2$, $CF_2CFCl$, $CF_2CF(CF_3)$ or $CF_2CH_2$; n is 0 or an integer of 1 to 1,000), $CF_2=CH(Rf^B)_n—F$ ($Rf^B$ is $CF_2CF_2$, $CF_2CFCl$, $CF_2CF(CF_3)$ or $CF_2CH_2$; n is 0 or an integer of 1 to 1,000), $CF_2=CF(Rf^B)_n—Br$ ($Rf^B$ is $CF_2CF_2$, $CF_2CFCl$, $CF_2CF(CF_3)$ or $CF_2CH_2$; n is 0 or an integer of 1 to 1,000), $CF_2=CH(Rf^B)_n—Br$ ($Rf^B$ is $CF_2CF_2$, $CF_2CFCl$, $CF_2CF(CF_3)$ or $CF_2CH_2$; n is 0 or an integer of 1 to 1,000), $CF_2=CF(Rf^B)_n—Cl$ ($Rf^B$ is $CF_2CF_2$, $CF_2CFCl$, $CF_2CF(CF_3)$ or $CF_2CH_2$; n is 0 or an integer of 1 to 1,000), $CF_2=CH(Rf^B)_n—Cl$ ($Rf^B$ is $CF_2CF_2$, $CF_2CFCl$, $CF_2CF(CF_3)$ or $CF_2CH_2$; n is 0 or an integer of 1 to 1,000), $CF_2=CF(Rf^B)_n—I$ ($Rf^B$ is $CF_2CF_2$, $CF_2CFCl$, $CF_2CF(CF_3)$ or $CF_2CH_2$; n is 0 or an integer of 1 to 1,000) and $CF_2=CH(Rf^B)_n—I$ ($Rf^B$ is $CF_2CF_2$, $CF_2CFCl$, $CF_2CF(CF_3)$ or $CF_2CH_2$; n is 0 or an integer of 1 to 1,000); fluorine-containing vinyl ethers such as $CF_2=CFOR$ (R is an alkyl group which may be substituted by halogen atom), $CF_2=C(CF_3)OR$ (R is an alkyl group which may be substituted by halogen atom), $(CF_3)_2C=CFOR$ (R is an alkyl group which may be substituted by halogen atom), $CF_2=CF[OCF_2CF(CF_3)]_nOC_3F_7$ (n is 0 or an integer of 1 to 20), $CF_2=CF[OCF_2CF(CF_3)]_nOCF_2CF=CF_2$ (n is 0 or an integer of 1 to 20), $CF_2=CF[OCF_2CF(CF_3)]_nOCF_2CFClCF_2Cl$ (n is 0 or an integer of 1 to 20), $CF_2=CF[OCF_2CF(CF_3)]_nOCF_2CF_2CF=CF_2$ (n is 0 or an integer of 1 to 20), $CF_2=CF[OCF_2CF(CF_3)]_nOCF_2CF_2CF=CH_2$ (n is 0 or an integer of 1 to 20), $CF_2=CF[OCF_2CF(CF_3)]_nOCF_2CF_2SO_3M$ (M is Li, Na, K, Rb, Cs, BeCl, MgCl, MgBr, MgI, MgNO_3, MgBF_4, MgPF_6, CaCl, CaBr, CaI, CaNO_3, CaBF_4, CaPF_6, FeCl_2, FeBr_2, FeI_2, CoCl, CoBr, CoI, ZnCl, ZnBr, ZnI, NiCl, NiBr, NiI, Ag, Cu, CuCl, CuBr, CuI, AuCl_2, AuBr_2 or AuI_2; n is 0 or an integer of 1 to 20), $CF_2=CF[OCF_2CF(CF_3)]_nO(CF_2)_mCO_2R$ (m is an integer of 1 to 10; n is 0 or an integer of 1 to 20; R is an alkyl group which may be substituted by hydrogen atom or halogen atom), $CF_2=CF[OCF_2CF(CF_3)]_nO(CF_2)_mCH_2OR$ (m is an integer of 1 to 10; n is 0 or an integer of 1 to 20; R is hydrogen atom or an alkyl group which may be substituted by hydrogen atom or halogen atom) and $CF_2=CF[OCF_2CF(CF_3)]_nO(CF_2)_m—I$ (m is an integer of 1 to 10; n is 0 or an integer of 1 to 20); fluorine-containing unsaturated carboxylic acids or esters thereof such as $CF_2=CY(CX_2)_nCOOR$ (X is H or F; Y is H, F or $CF_3$; n is 0 or an integer of 1 to 20; R is an alkyl group which may be substituted by hydrogen atom or halogen atom); fluorine-containing unsaturated sulfonates such as $CF_2=CF(CX_2)_nCH_2OR$ (X is H or F; n is 0 or an integer of 1 to 20; R is hydrogen atom or an alkyl group which may be substituted by hydrogen atom or halogen atom), $CF_2=CY—C_6X_4—CO_2R$ (X is H or F; Y is H, F or $CF_3$; R is an alkyl group which may be substituted by hydrogen atom or halogen atom) and $CF_2=CY—C_6X_4—SO_3M$ (X is H or F; Y is H, F or $CF_3$; M is Li, Na, K, Rb, Cs, BeCl, MgCl, MgBr, MgI, MgNO_3, MgBF_4, MgPF_6, CaCl, CaBr, CaI, CaNO_3, CaBF_4, CaPF_6, FeCl_2, FeBr_2, FeI_2, CoCl, CoBr, CoI, ZnCl, ZnBr, ZnI, NiCl, NiBr, NiI, Ag, Cu, CuCl, CuBr, CuI, AuCl_2, AuBr_2 or AuI_2), and $CF_2=CY—C_6X_4—CH_2OR$ (X is H or F; Y is H, F or $CF_3$; R is hydrogen atom or an alkyl group which may be substituted by hydrogen atom or halogen atom).

In the first preparation process of the present invention, the heteroaromatic ring compound (A) having a N—H group is allowed to react with the fluoroalkene (B) in the absence of alkali metal.

The first preparation process differs from the preparation processes of subjecting a heteroaromatic ring compound to reaction in the form of an alkali metal salt which are disclosed in V. V. Rudyuk et al., J. Fluorine Chem., 125, pp. 1465-1471 (2004), D. C. England et al., J. Am. Chem. Soc., 82, pp. 5116-5122 (1960) and U.S. Pat. No. 2,861,990 because in the present invention, the heteroaromatic ring compound (A) having a N—H group is subjected to reaction, and also differs from the reactions disclosed in V. V. Rudyuk et al., J. Fluorine Chem., 125, pp. 1465-1471 (2004), D. C. England et al., J. Am. Chem. Soc., 82, pp. 5116-5122 (1960) and U.S. Pat. No. 2,861,990 because in the present invention, even in the case of using the heteroaromatic ring compound (A) having a N—H group as a starting material, reaction is carried out in the absence of alkali metal.

In the preparation process of the present invention, a metal which is not allowed to be present in a reaction system is alkali metal, and also presence of other metal being capable of taking part in the reaction directly or as a catalyst is not necessary. Also it is not especially necessary to allow a metal to be present even in the form of a salt or a complex.

The reaction may be carried out in a solution of the heteroaromatic ring compound (A) or in a molten state of the heteroaromatic ring compound (A).

When the reaction is carried out in the solution, it proceeds even without using a catalyst by making the heteroaromatic ring compound (A) in a homogeneous liquid state.

Examples of a usable reaction solvent are, for instance, diethyl ether, t-butyl methyl ether, diisopropyl ether, dibutyl ether, tetrahydrofuran, dioxane, dimethoxymethane, dimethoxyethane, diglyme, triglyme, tetraglyme, N,N-dimethylformamide, N,N-dimethylacetamide, N-methylpyrrolidone, ethyl acetate, methyl acetate, propyl acetate, butyl acetate, dimethyl sulfoxide, sulfolane, hexamethylphosphoric triamide, benzene, toluene, xylene, chloroform, methylene chloride, dichloroethane, trichloroethane, dichloropentafluoropropane, dichlorofluoroethane, trichlorotrifluoroethane, tetrachlorohexafluorobutane, dichlorooctafluorobutane, pentachloropentafluorohexane, dibromotetrafluoroethane, perfluorohexane, perfluoro(butyltetrahydrofuran) and perfluorotributylamine. From the viewpoint of solubility of the heteroaromatic ring compound, preferable are diethyl ether, t-butyl methyl ether, dibutyl ether, diisopropyl ether, tetrahydrofuran, dioxane, dimethoxyethane, diglyme, triglyme, tetraglyme, N,N-dimethylformamide, N,N-dimethylacetamide, N-methylpyrrolidone, ethyl acetate, methyl acetate, propyl acetate, butyl acetate, dimethyl sulfoxide and sulfolane.

A concentration of the solution may be optionally selected depending on kind of the heteroaromatic ring compound, kind of a solvent, kind of the fluoroalkene and a reaction temperature. As far as a part thereof is homogeneously dissolved, a higher concentration is preferable. The concentration is preferably not less than 30% by mass, further preferably not less than 60% by mass.

A reaction pressure is not limited particularly. The reaction proceeds at any pressure as far as the fluoroalkene can contact with the solution containing the heteroaromatic ring compound.

In the present invention, it is especially preferable that the reaction is conducted in the absence of a solvent with the heteroaromatic ring compound (A) being in a molten state, from the viewpoint that no operation for separating a solvent is necessary and production cost is decreased.

In the present invention, the molten state of the heteroaromatic ring compound encompasses not only a molten state of the heteroaromatic ring compound alone but also a molten state of the heteroaromatic ring compound alone at a temperature less than its melting point by blending a melting point depressor.

Examples of a melting point depressor are the above-mentioned reaction solvents which are used in an amount being capable of dissolving or swelling the heteroaromatic ring compound.

In the case where the reaction is conducted in a molten state, the reaction temperature is a melting point of the heteroaromatic ring compound (A) (or a reduced melting point) or more and less than its decomposition temperature.

The reaction pressure is not limited particularly. The reaction proceeds at any pressure as far as the fluoroalkene can contact with the molten substance containing the heteroaromatic ring compound.

A method of introducing the fluoroalkene (B) to a reaction system is not limited particularly. For example, there can be preferably employed a method of introducing gasified fluoroalkene under pressure to the solution of the heteroaromatic ring compound (A) or to the heteroaromatic ring compound (A) in a molten state, or a method of adding dropwise fluoroalkene to the solution of the heteroaromatic ring compound (A) or to the heteroaromatic ring compound (A) in a molten state.

The heteroaromatic ring compound (C) having a N—Rf group in its ring which is obtained in the first preparation process is a compound obtained by adding the fluoroalkene (B) to the N—H group of the heteroaromatic ring compound (A) having a N—H group in its ring. This compound is a fluorine-containing heteroaromatic ring compound represented by the formula (C1):

wherein

is as defined in the formula (A1); Rf is as defined in the formula (c).

Accordingly, the above-mentioned fluorine-containing heteroaromatic ring compound (C) is a compound obtained by converting the N—H group of the heteroaromatic ring compound (A) to the N—Rf group. For example, a compound having an imidazole skeleton having N—H group in its ring, a compound having a pyrrole skeleton having N—H group in its ring, a compound having a pyrazole skeleton having N—H group in its ring, a compound having a triazole skeleton having N—H group in its ring, a compound having an indole skeleton having N—H group in its ring, a compound having a purine skeleton having N—H group in its ring and a purine derivative having N—H group in its ring are formed into a compound having an imidazole skeleton having N—Rf group in its ring, a compound having a pyrrole skeleton having N—Rf group in its ring, a compound having a pyrazole skeleton having N—Rf group in its ring, a compound having a triazole skeleton having N—Rf group in its ring, a compound having an indole skeleton having N—Rf group in its ring, a compound having a purine skeleton having N—Rf group in its ring and a purine derivative having N—Rf group in its ring, respectively.

Examples of the heteroaromatic ring compound (C1) represented by the above-mentioned formula (C1) are a fluorine-containing imidazole compound represented by the formula (C1-1):

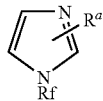

wherein $R^a$s are the same or different, and each is halogen atom, a functional group or an organic group and may be present or may not be present, and when $R^a$s are present, the whole or a part of hydrogen atoms of the heteroaromatic ring are substituted by them; Rf is $Rf^1$ where $Rf^1$ is the same as the formula (c) or is a monovalent organic group which may have at least one residue defined by deleting Rf group from the formula (C1-1), a fluorine-containing pyrrole compound represented by the formula (C1-2):

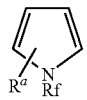

wherein $R^a$s are the same or different, and each is halogen atom, a functional group or an organic group and may be present or may not be present, and when $R^a$s are present, the whole or a part of hydrogen atoms of the heteroaromatic ring are substituted by them; Rf is $Rf^2$ where $Rf^2$ is the same as the formula (c) or is a monovalent organic group which may have at least one residue defined by deleting Rf group from the formula (C1-2), a fluorine-containing pyrazole compound represented by the formula (C1-3):

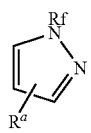

wherein $R^a$s are the same or different, and each is halogen atom, a functional group or an organic group and may be present or may not be present, and when $R^a$s are present, the whole or a part of hydrogen atoms of the heteroaromatic ring are substituted by them; Rf is $Rf^3$ where $Rf^3$ is the same as the formula (c) or is a monovalent organic group which may have at least one residue defined by deleting Rf group from the formula (C1-3), a fluorine-containing triazole compound represented by the formula (C1-4):

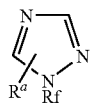

wherein $R^a$s are the same or different, and each is halogen atom, a functional group or an organic group and may be present or may not be present, and when $R^a$s are present, the whole or a part of hydrogen atoms of the heteroaromatic ring are substituted by them; Rf is $Rf^4$ where $Rf^4$ is the same as the formula (c) or is a monovalent organic group which may have at least one residue defined by deleting Rf group from the formula (C1-4), a fluorine-containing indole compound represented by the formula (C1-5):

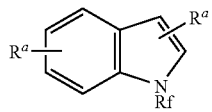

wherein $R^a$s are the same or different, and each is halogen atom, a functional group or an organic group and may be present or may not be present, and when $R^a$s are present, the whole or a part of hydrogen atoms of the heteroaromatic ring and/or the aromatic ring are substituted by them; Rf is $Rf^5$ where $Rf^5$ is the same as the formula (c) or is a monovalent organic group which may have at least one residue defined by deleting Rf group from the formula (C1-5), a fluorine-containing purine compound represented by the formula (C1-6):

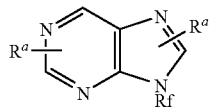

wherein $R^a$s are the same or different, and each is halogen atom, a functional group or an organic group and may be present or may not be present, and when $R^a$s are present, the whole or a part of hydrogen atoms of the heteroaromatic ring and/or the aromatic ring are substituted by them; Rf is $Rf^6$ where $Rf^6$ is the same as the formula (c) or is a monovalent organic group which may have at least one residue defined by deleting Rf group from the formula (C1-6), and a fluorine-containing purine derivative represented by the formula (C1-7):

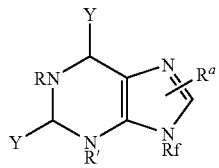

wherein $R^a$ is halogen atom, a functional group or an organic group and may be present or may not be present; Ys are the same or different and each is =O, —NRR', —OR, F or $F_2$; R and R' are the same or different and each is hydrogen atom, an alkyl group, an arylalkyl group, an organosilicon group, an alkoxyl group or a carboxyester group; Rf is $Rf^7$ where $Rf^7$ is the same as the formula (c) or is a monovalent organic group which may have at least one residue defined by deleting Rf group from the formula (C1-7), and examples of the substituent groups thereof are those concretely exemplified in the heteroaromatic ring compound (A1) and the fluoroalkene (B).

Examples of the heteroaromatic ring compound (C) having N—Rf group in its ring are fluorine-containing imidazole compounds shown in Table 14, fluorine-containing pyrrole compounds shown in Table 15, fluorine-containing pyrazole compounds shown in Table 16, fluorine-containing triazole compounds shown in Table 17, fluorine-containing indole compounds shown in Table 18, fluorine-containing purine compounds shown in Table 19, fluorine-containing purine derivatives shown in Table 20, fluorine-containing benzimidazole compounds shown in Table 21, fluorine-containing 1,2,3-triazole compounds shown in Table 22, fluorine-containing tetrazole compounds shown in Table 23, fluorine-containing isoindole compounds shown in Table 24, fluorine-containing indazole compounds shown in Table 25, and fluorine-containing benzotriazole compounds shown in Table 26.

In the following Tables 14 to 26, definitions of each substituent are effective only in the corresponding tables. Figures showing the number of atoms are not represented especially by small letters. Further Ph, i and n are abbreviations of phenyl, iso and normal, respectively.

TABLE 14

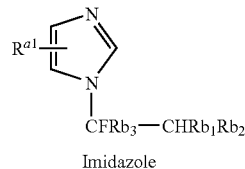

Imidazole

| Compound No. | $R^{a1}$ | Rb1 | | Rb2 | Rb3 |
|---|---|---|---|---|---|
| C1-1-1 | H | H | H | F | F | F |
| 2 | H | H | H | F | CF3 | F |
| 3 | H | H | H | F | OCF3 | F |
| 4 | H | H | H | H | H | F |
| 5 | H | H | H | CF3 | CF3 | F |
| 6 | H | H | H | CF3 | CF3 | OCH3 |
| 7 | H | H | H | COOR | F | F |
| 8 | H | H | H | COOR | CF3 | F |
| 9 | H | H | H | CF2COOR | F | F |
| 10 | H | H | H | CF2CH2OR | F | F |
| 11 | H | H | H | CF2CF(CF3)2 | F | F |
| 12 | H | H | H | F | CF(CF3)2 | CF3 |
| 13 | H | H | H | CF3 | F | CF(CF3)2 |
| 14 | H | H | H | OAlkyl | F | F |
| 15 | H | H | H | F | [OCF2CF(CF3)]nOC3F7 | F |
| 16 | H | H | H | F | [OCF2CF(CF3)]nOCF2CF=CH2 | F |
| 17 | H | H | H | F | [OCF2CF(CF3)]nOCF2CFClCF2Cl | F |
| 18 | H | H | H | F | [OCF2CF(CF3)]nO(CF2)mCFClCF2Cl | F |
| 19 | H | H | H | F | [OCF2CF(CF3)]nO(CF2)m] | F |
| 20 | H | H | H | F | [OCF2CF(CF3)]nOCF2CF2SO2R | F |
| 21 | H | H | H | F | [OCF2CF2]nO(CF2)mCFClCF2Cl | F |
| 22 | H | H | H | F | [OCF2CF2]nO(CF2)mF | F |
| 23 | H | H | H | H | (CF2)nF | F |
| 24 | H | H | H | H | (CF2)nI | F |
| 25 | H | H | H | F | Cl | F |
| 26 | CH3 | H | H | F | F | F |
| 27 | CH3 | H | H | F | CF3 | F |
| 28 | CH3 | CH3 | H | F | F | F |
| 29 | CH3 | CH3 | H | F | CF3 | F |
| 30 | Ph | H | H | F | F | F |
| 31 | Ph | H | H | F | CF3 | F |
| 32 | CH3 | Ph | H | F | F | F |
| 33 | CH3 | Ph | H | F | CF3 | F |
| 34 | CH2OR | H | H | F | F | F |
| 35 | CH2OR | H | H | F | CF3 | F |
| 36 | COOR | H | H | F | F | F |
| 37 | COOR | H | H | F | CF3 | F |
| 38 | Cl | H | H | F | F | F |
| 39 | Cl | H | H | F | CF3 | F |
| 40 | C4H9 | CH2OR | Cl | F | F | F |
| 41 | C4H9 | CH2OR | Cl | F | CF3 | F |
| 42 | CH2CH(NRR')COOR | H | H | F | F | F |
| 43 | CH2CH(NRR')COOR | H | H | F | CF3 | F |
| 44 | CH2CH(NRR')COOR | F | H | F | F | F |
| 45 | CH2CN | H | H | F | F | F |
| 46 | CH2CN | H | H | F | CF3 | F |
| 47 | CH2CN | F | H | F | F | F |
| 48 | CH2COOH | H | H | F | F | F |
| 49 | CH2COOH | H | H | F | CF3 | F |
| 50 | CH2COOH | F | H | F | F | F |

TABLE 15

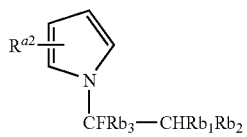

Pyrrole

| Compound No. | $R^{a2}$ | | | | Rb1 | Rb2 | Rb3 |
|---|---|---|---|---|---|---|---|
| C1-2-1 | H | H | H | H | F | F | F |
| 2 | H | H | H | H | F | CF3 | F |
| 3 | H | H | H | H | F | OCF3 | F |
| 4 | H | H | H | H | H | H | F |
| 5 | H | H | H | H | CF3 | CF3 | F |
| 6 | H | H | H | H | CF3 | CF3 | OCH3 |
| 7 | H | H | H | H | COOR | F | F |
| 8 | H | H | H | H | COOR | CF3 | F |
| 9 | H | H | H | H | CF2COOR | F | F |
| 10 | H | H | H | H | CF2CH2OR | F | F |
| 11 | H | H | H | H | CF2CF(CF3)2 | F | F |
| 12 | H | H | H | H | F | CF(CF3)2 | CF3 |
| 13 | H | H | H | H | CF3 | F | CF(CF3)2 |
| 14 | H | H | H | H | OAlkyl | F | F |
| 15 | H | H | H | H | F | [OCF2CF(CF3)]nOC3F7 | F |
| 16 | H | H | H | H | F | [OCF2CF(CF3)]nOCF2CF=CH2 | F |
| 17 | H | H | H | H | F | [OCF2CF(CF3)]nOCF2CFClCF2Cl | F |
| 18 | H | H | H | H | F | [OCF2CF(CF3)]nO(CF2)mCFClCF2Cl | F |
| 19 | H | H | H | H | F | [OCF2CF(CF3)]nO(CF2)mI | F |
| 20 | H | H | H | H | F | [OCF2CF(CF3)]nOCF2CF2SO2R | F |
| 21 | H | H | H | H | F | [OCF2CF2]nO(CF2)mCFClCF2Cl | F |
| 22 | H | H | H | H | F | [OCF2CF2]nO(CF2)mF | F |
| 23 | H | H | H | H | H | (CF2)nF | F |
| 24 | H | H | H | H | H | (CF2)nI | F |
| 25 | H | H | H | H | F | Cl | F |
| 26 | CH3 | H | H | H | F | F | F |
| 27 | CH3 | H | H | H | F | CF3 | F |
| 28 | Ph | H | H | H | F | F | F |
| 29 | Ph | H | H | H | F | CF3 | F |
| 30 | CH3 | Ph | H | H | F | F | F |
| 31 | CH3 | Ph | H | H | F | CF3 | F |
| 32 | CH2OR | H | H | H | F | F | F |
| 33 | CH2OR | H | H | H | F | CF3 | F |
| 34 | COOR | H | H | H | F | F | F |
| 35 | COOR | H | H | H | F | CF3 | F |
| 36 | Cl | H | H | H | F | F | F |
| 37 | Cl | H | H | H | F | CF3 | F |
| 38 | CH(NRR')COOR | H | H | H | F | F | F |
| 39 | CH(NRR')COOR | H | H | H | F | CF3 | F |
| 40 | CH(NRR')COOR | F | H | H | F | F | F |
| 41 | CH(NRR')COOR | F | H | H | F | CF3 | F |
| 42 | CH2CH2NRR' | H | H | H | F | F | F |
| 43 | CH2CH2NRR' | H | H | H | F | CF3 | F |
| 44 | CH2CN | H | H | H | F | F | F |
| 45 | CH2CN | F | H | H | F | CF3 | F |
| 46 | CH2COOH | H | H | H | F | F | F |
| 47 | CH2COOH | F | H | H | F | CF3 | F |

TABLE 16

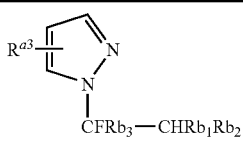

Pyrazole

| Compound No. | $R^{a3}$ | | | Rb1 | Rb2 | Rb3 |
|---|---|---|---|---|---|---|
| C-1-3-1 | H | H | H | F | F | F |
| 2 | H | H | H | F | CF3 | F |
| 3 | H | H | H | F | OCF3 | F |
| 4 | H | H | H | H | H | F |
| 5 | H | H | H | CF3 | CF3 | F |

TABLE 16-continued

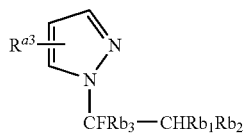

Pyrazole

| Compound No. | $R^{a3}$ | | | Rb1 | Rb2 | Rb3 |
|---|---|---|---|---|---|---|
| 6 | H | H | H | CF3 | CF3 | OCH3 |
| 7 | H | H | H | COOR | F | F |
| 8 | H | H | H | COOR | CF3 | F |
| 9 | H | H | H | CF2COOR | F | F |
| 10 | H | H | H | CF2CH2OR | F | F |
| 11 | H | H | H | CF2CF(CF3)2 | F | F |
| 12 | H | H | H | F | CF(CF3)2 | CF3 |
| 13 | H | H | H | CF3 | F | CF(CF3)2 |
| 14 | H | H | H | OAlkyl | F | F |
| 15 | H | H | H | F | [OCF2CF(CF3)]nOC3F7 | F |
| 16 | H | H | H | F | [OCF2CF(CF3)]nOCF2CF=CH2 | F |
| 17 | H | H | H | F | [OCF2CF(CF3)]nOCF2CFClCF2Cl | F |
| 18 | H | H | H | F | [OCF2CF(CF3)]nO(CF2)mCFClCF2Cl | F |
| 19 | H | H | H | F | [OCF2CF(CF3)]nO(CF2)mI | F |
| 20 | H | H | H | F | [OCF2CF(CF3)]nOCF2CF2SO2R | F |
| 21 | H | H | H | F | [OCF2CF2]nO(CF2)mCFClCF2Cl | F |
| 22 | H | H | H | F | [OCF2CF2]nO(CF2)mF | F |
| 23 | H | H | H | H | (CF2)nF | F |
| 24 | H | H | H | H | (CF2)nI | F |
| 25 | H | H | H | F | Cl | F |
| 26 | CH3 | H | H | F | F | F |
| 27 | CH3 | H | H | F | CF3 | F |
| 28 | CH3 | CH3 | H | F | F | F |
| 29 | CH3 | CH3 | H | F | CF3 | F |
| 30 | Ph | H | H | F | F | F |
| 31 | Ph | H | H | F | CF3 | F |
| 32 | CH3 | Ph | H | F | F | F |
| 33 | CH3 | Ph | H | F | CF3 | F |
| 34 | CH2OR | H | H | F | F | F |
| 35 | CH2OR | H | H | F | CF3 | F |
| 36 | COOR | H | H | F | F | F |
| 37 | COOR | H | H | F | CF3 | F |
| 38 | Cl | H | H | F | F | F |
| 39 | Cl | H | H | F | CF3 | F |

TABLE 17

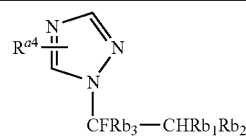

Triazole

| Compound No. | $R^{a4}$ | | Rb1 | Rb2 | Rb3 |
|---|---|---|---|---|---|
| C1-4-1 | H | H | F | F | F |
| 2 | H | H | F | CF3 | F |
| 3 | H | H | F | OCF3 | F |
| 4 | H | H | H | H | F |
| 5 | H | H | CF3 | CF3 | F |
| 6 | H | H | CF3 | CF3 | OCH3 |
| 7 | H | H | COOR | F | F |
| 8 | H | H | COOR | CF3 | F |
| 9 | H | H | CF2COOR | F | F |
| 10 | H | H | CF2CH2OR | F | F |
| 11 | H | H | CF2CF(CF3)2 | F | F |
| 12 | H | H | F | CF(CF3)2 | CF3 |
| 13 | H | H | CF3 | F | CF(CF3)2 |
| 14 | H | H | OAlkyl | F | F |
| 15 | H | H | F | [OCF2CF(CF3)]nOC3F7 | F |
| 16 | H | H | F | [OCF2CF(CF3)]nOCF2CF=CH2 | F |
| 17 | H | H | F | [OCF2CF(CF3)]nOCF2CFClCF2Cl | F |
| 18 | H | H | F | [OCF2CF(CF3)]nO(CF2)mCFClCF2Cl | F |

TABLE 17-continued

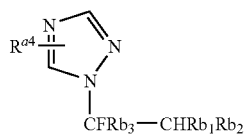

Triazole

| Compound No. | $R^{a4}$ | Rb1 | Rb2 | Rb3 |
|---|---|---|---|---|
| 19 | H | H | F | [OCF2CF(CF3)]nO(CF2)mI | F |
| 20 | H | H | F | [OCF2CF(CF3)]nOCF2CF2SO2R | F |
| 21 | H | H | F | [OCF2CF2]nO(CF2)mCFClCF2Cl | F |
| 22 | H | H | F | [OCF2CF2]nO(CF2)mF | F |
| 23 | H | H | H | (CF2)nF | F |
| 24 | H | H | H | (CF2)nI | F |
| 25 | H | H | F | Cl | F |
| 26 | CH3 | H | F | F | F |
| 27 | CH3 | H | F | CF3 | F |
| 28 | Ph | H | F | F | F |
| 29 | Ph | H | F | CF3 | F |
| 30 | COOR | H | F | F | F |
| 31 | COOR | H | F | CF3 | F |
| 32 | Cl | H | F | F | F |
| 33 | Cl | H | F | CF3 | F |

TABLE 18

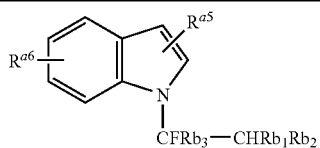

Indole

| Compound No. | $R^{a6}$ | | | | $R^{a5}$ | | Rb1 | Rb2 | Rb3 |
|---|---|---|---|---|---|---|---|---|---|
| C1-5-1 | H | H | H | H | H | H | F | F | F |
| 2 | H | H | H | H | H | H | F | CF3 | F |
| 3 | H | H | H | H | H | H | H | H | F |
| 4 | H | H | H | H | H | H | CF3 | CF3 | F |
| 5 | H | H | H | H | H | H | CF3 | CF3 | OCH3 |
| 6 | F | H | H | H | H | H | F | F | F |
| 7 | F | H | H | H | H | H | F | CF3 | F |
| 8 | COOR | H | H | H | H | H | F | F | F |
| 9 | COOR | H | H | H | H | H | F | CF3 | F |
| 10 | COOR | F | H | H | H | H | F | F | F |
| 11 | COOR | F | H | H | H | H | F | CF3 | F |
| 12 | H | H | H | H | COOR | H | F | F | F |
| 13 | H | H | H | H | COOR | H | F | CF3 | F |
| 14 | F | H | H | H | COOR | H | F | F | F |
| 15 | F | H | H | H | COOR | H | F | CF3 | F |
| 16 | H | H | H | H | CH(NRR')COOR | H | F | F | F |
| 17 | H | H | H | H | CH(NRR')COOR | H | F | CF3 | F |
| 18 | F | H | H | H | CH(NRR')COOR | H | F | F | F |
| 19 | F | H | H | H | CH(NRR')COOR | H | F | CF3 | F |
| 20 | H | H | H | H | CH2NRR' | H | F | F | F |
| 21 | H | H | H | H | CH2NRR' | H | F | CF3 | F |
| 22 | F | H | H | H | CH2NRR' | H | F | F | F |
| 23 | F | H | H | H | CH2NRR' | H | F | CF3 | F |
| 24 | H | H | H | H | CN | H | F | F | F |
| 25 | H | H | H | H | CN | H | F | CF3 | F |
| 26 | F | H | H | H | CN | H | F | F | F |
| 27 | F | H | H | H | CN | H | F | CF3 | F |

TABLE 19

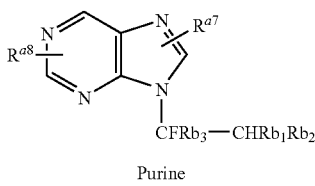

Purine

| Compound No. | $R^{a8}$ | $R^{a7}$ | Rb1 | Rb2 | Rb3 |
|---|---|---|---|---|---|
| C1-6-1 | H | H | H | F | F | F |
| 1 | H | H | H | F | CF3 | F |
| 2 | H | H | H | H | H | F |
| 3 | H | H | CF3 | CF3 | F |
| 4 | H | H | CF3 | CF3 | OCH3 |
| 5 | COOR | H | H | F | F | F |
| 6 | COOR | H | H | F | CF3 | F |
| 7 | COOR | F | H | F | F | F |
| 8 | COOR | F | H | F | CF3 | F |
| 9 | CH3 | H | H | F | F | F |
| 10 | CH3 | H | H | F | CF3 | F |
| 11 | CH3 | F | H | F | F | F |
| 12 | CH3 | F | H | F | CF3 | F |
| 13 | Ph | H | H | F | F | F |
| 14 | Ph | H | H | F | CF3 | F |
| 15 | Ph | F | H | F | F | F |
| 16 | Ph | F | H | F | CF3 | F |
| 17 | NR2 | H | H | F | F | F |
| 18 | NR2 | H | H | F | CF3 | F |
| 19 | OR | H | H | F | F | F |
| 20 | OR | H | H | F | CF3 | F |

TABLE 20

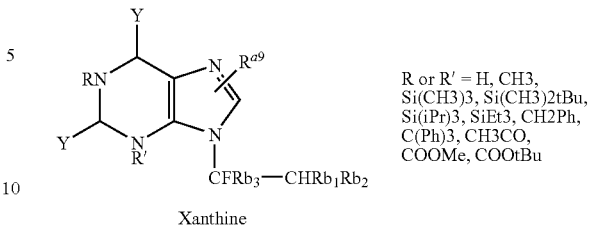

R or R' = H, CH3, Si(CH3)3, Si(CH3)2tBu, Si(iPr)3, SiEt3, CH2Ph, C(Ph)3, CH3CO, COOMe, COOtBu

Xanthine

| Compound No. | Y | $R^{a9}$ | Rb1 | Rb2 | Rb3 |
|---|---|---|---|---|---|
| C1-7-1 | =O | =O | H | F | F | F |
| 2 | =O | =O | H | F | CF3 | F |
| 3 | =O | =O | H | H | H | F |
| 4 | =O | =O | H | CF3 | CF3 | F |
| 5 | =O | =O | H | CF3 | CF3 | OCH3 |
| 6 | =O | =O | CH3 | F | F | F |
| 7 | =O | =O | CH3 | F | CF3 | F |
| 8 | =O | =O | Ph | F | F | F |
| 9 | =O | =O | Ph | F | CF3 | F |
| 10 | =O | =O | OR | F | F | F |
| 11 | =O | =O | OR | F | CF3 | F |
| 12 | =O | =O | F | F | F | F |
| 13 | =O | =O | F | F | CF3 | F |
| 14 | =O | NRR' | H | F | F | F |
| 15 | =O | NRR' | H | F | CF3 | F |
| 16 | =O | NRR' | F | F | F | F |
| 17 | =O | NRR' | F | F | CF3 | F |
| 18 | =O | OR | H | F | F | F |
| 19 | =O | OR | H | F | CF3 | F |
| 20 | =O | F | H | F | F | F |
| 21 | =O | F | H | F | CF3 | F |
| 22 | =O | F | CH3 | F | F | F |
| 23 | =O | F | CH3 | F | CF3 | F |

TABLE 20-continued

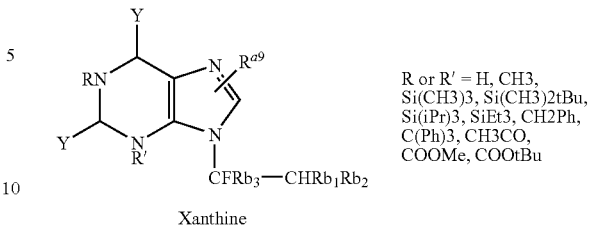

R or R' = H, CH3, Si(CH3)3, Si(CH3)2tBu, Si(iPr)3, SiEt3, CH2Ph, C(Ph)3, CH3CO, COOMe, COOtBu

Xanthine

| Compound No. | Y | $R^{a9}$ | Rb1 | Rb2 | Rb3 |
|---|---|---|---|---|---|
| 24 | =O | F2 | H | F | F | F |
| 25 | =O | F2 | H | F | CF3 | F |
| 26 | =O | F2 | CH3 | F | F | F |
| 27 | =O | F2 | CH3 | F | CF3 | F |
| 28 | =O | F2 | Ph | F | F | F |
| 29 | =O | F2 | Ph | F | CF3 | F |
| 30 | =O | F2 | OR | F | F | F |
| 31 | =O | F2 | OR | F | CF3 | F |

TABLE 21

Benzimidazole

| Compound No. | $R^{a11}$ | | | | $R^{a10}$ | Rb1 | Rb2 | Rb3 |
|---|---|---|---|---|---|---|---|---|
| C1-8-1 | H | H | H | H | H | F | F | F |
| 2 | H | H | H | H | H | F | CF3 | F |
| 3 | H | H | H | H | H | H | H | F |
| 4 | H | H | H | H | H | CF3 | CF3 | F |
| 5 | H | H | H | H | H | CF3 | CF3 | OCH3 |
| 6 | COOR | H | H | H | H | F | F | F |
| 7 | COOR | H | H | H | H | F | CF3 | F |
| 8 | COOR | F | H | H | H | F | F | F |
| 9 | COOR | F | H | H | H | F | CF3 | F |
| 10 | CH3 | H | H | H | H | F | F | F |
| 11 | CH3 | H | H | H | H | F | CF3 | F |
| 12 | CH3 | F | H | H | H | F | F | F |
| 13 | CH3 | F | H | H | H | F | CF3 | F |
| 14 | Ph | H | H | H | H | F | F | F |
| 15 | Ph | H | H | H | H | F | CF3 | F |
| 16 | Ph | F | H | H | H | F | F | F |
| 17 | Ph | F | H | H | H | F | CF3 | F |
| 18 | H | H | H | H | COOR | F | F | F |
| 19 | H | H | H | H | COOR | F | CF3 | F |
| 20 | H | H | H | H | CN | F | F | F |
| 21 | H | H | H | H | CN | F | CF3 | F |

TABLE 22

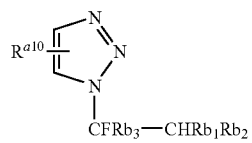

Triazole

| Compound No. | $R^{a10}$ | Rb1 | Rb2 | Rb3 |
|---|---|---|---|---|
| C1-9-1 | H | H | F | F | F |
| 2 | H | H | F | CF3 | F |
| 3 | H | H | F | OCF3 | F |
| 4 | H | H | H | H | F |
| 5 | H | H | CF3 | CF3 | F |
| 6 | H | H | CF3 | CF3 | OCH3 |
| 7 | H | H | COOR | F | F |
| 8 | H | H | COOR | CF3 | F |
| 9 | H | H | CF2COOR | F | F |
| 10 | H | H | CF2CH2OR | F | F |
| 11 | H | H | CF2CF(CF3)2 | F | F |
| 12 | H | H | F | CF(CF3)2 | CF3 |
| 13 | H | H | CF3 | F | CF(CF3)2 |
| 14 | H | H | OAlkyl | F | F |
| 15 | H | H | F | [OCF2CF(CF3)]nOC3F7 | F |
| 16 | H | H | F | [OCF2CF(CF3)]nOCF2CF=CH2 | F |
| 17 | H | H | F | [OCF2CF(CF3)]nOCF2CFClCF2Cl | F |
| 18 | H | H | F | [OCF2CF(CF3)]nO(CF2)mCFClCF2Cl | F |
| 19 | H | H | F | [OCF2CF(CF3)]nO(CF2)mI | F |
| 20 | H | H | F | [OCF2CF(CF3)]nOCF2CF2SO2R | F |
| 21 | H | H | F | [OCF2CF2]nO(CF2)mCFClCF2Cl | F |
| 22 | H | H | F | [OCF2CF2]nO(CF2)mF | F |
| 23 | H | H | H | (CF2)nF | F |
| 24 | H | H | H | (CF2)nI | F |
| 25 | H | H | F | Cl | F |
| 26 | CH3 | H | F | F | F |
| 27 | CH3 | H | F | CF3 | F |
| 28 | Ph | H | F | F | F |
| 29 | Ph | H | F | CF3 | F |
| 30 | COOR | H | F | F | F |
| 31 | COOR | H | F | CF3 | F |
| 32 | Cl | H | F | F | F |
| 33 | Cl | H | F | CF3 | F |

TABLE 23

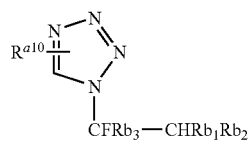

Tetrazole

| Compound No. | $R^{a10}$ | Rb1 | Rb2 | Rb3 |
|---|---|---|---|---|
| C1-10-1 | H | F | F | F |
| 2 | H | F | CF3 | F |
| 3 | H | F | OCF3 | F |
| 4 | H | H | H | F |
| 5 | H | CF3 | CF3 | F |
| 6 | H | CF3 | CF3 | OCH3 |
| 7 | H | COOR | F | F |
| 8 | H | COOR | CF3 | F |
| 9 | H | CF2COOR | F | F |
| 10 | H | CF2CH2OR | F | F |
| 11 | H | CF2CF(CF3)2 | F | F |
| 12 | H | F | CF(CF3)2 | CF3 |
| 13 | H | CF3 | F | CF(CF3)2 |
| 14 | H | OAlkyl | F | F |
| 15 | H | F | [OCF2CF(CF3)]nOC3F7 | F |
| 16 | H | F | [OCF2CF(CF3)]nOCF2CF=CH2 | F |
| 17 | H | F | [OCF2CF(CF3)]nOCF2CFClCF2Cl | F |
| 18 | H | F | [OCF2CF(CF3)]nO(CF2)mCFClCF2Cl | F |
| 19 | H | F | [OCF2CF(CF3)]nO(CF2)mI | F |

TABLE 23-continued

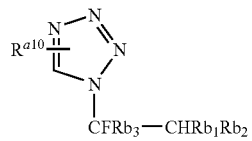

Tetrazole

| Compound No. | $R^{a10}$ | Rb1 | Rb2 | Rb3 |
|---|---|---|---|---|
| 20 | H | F | [OCF2CF(CF3)]nOCF2CF2SO2R | F |
| 21 | H | F | [OCF2CF2]nO(CF2)mCFClCF2Cl | F |
| 22 | H | F | [OCF2CF2]nO(CF2)mF | F |
| 23 | H | H | (CF2)nF | F |
| 24 | H | H | (CF2)nI | F |
| 25 | H | F | Cl | F |
| 26 | F | F | F | F |
| 27 | F | F | CF3 | F |
| 28 | CH3 | F | F | F |
| 29 | CH3 | F | CF3 | F |
| 30 | Ph | F | F | F |
| 31 | Ph | F | CF3 | F |
| 32 | COOR | F | F | F |
| 33 | COOR | F | CF3 | F |

TABLE 24

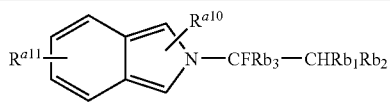

Isoindole

| Compound No. | $R^{a11}$ | | | | $R^{a10}$ | Rb1 | Rb2 | Rb3 |
|---|---|---|---|---|---|---|---|---|
| C1-11-1 | H | H | H | H | H | H | F | F | F |
| 2 | H | H | H | H | H | H | F | CF3 | F |
| 3 | H | H | H | H | H | H | H | H | F |
| 4 | H | H | H | H | H | H | CF3 | CF3 | F |
| 5 | H | H | H | H | H | H | CF3 | CF3 | OCH3 |
| 6 | F | H | H | H | H | H | F | F | F |
| 7 | F | H | H | H | H | H | F | CF3 | F |
| 8 | COOR | H | H | H | H | H | F | F | F |
| 9 | COOR | H | H | H | H | H | F | CF3 | F |
| 10 | COOR | F | H | H | H | H | F | F | F |
| 11 | COOR | F | H | H | H | H | F | CF3 | F |
| 12 | H | H | H | H | COOR | H | F | F | F |
| 13 | H | H | H | H | COOR | H | F | CF3 | F |
| 14 | F | H | H | H | COOR | H | F | F | F |
| 15 | F | H | H | H | COOR | H | F | CF3 | F |
| 16 | H | H | H | H | CH(NRR')COOR | H | F | F | F |
| 17 | H | H | H | H | CH(NRR')COOR | H | F | CF3 | F |
| 18 | F | H | H | H | CH(NRR')COOR | H | F | F | F |
| 19 | F | H | H | H | CH(NRR')COOR | H | F | CF3 | F |
| 20 | H | H | H | H | CH2NRR' | H | F | F | F |
| 21 | H | H | H | H | CH2NRR' | H | F | CF3 | F |
| 22 | F | H | H | H | CH2NRR' | H | F | F | F |
| 23 | F | H | H | H | CH2NRR' | H | F | CF3 | F |
| 24 | H | H | H | H | CN | H | F | F | F |
| 25 | H | H | H | H | CN | H | F | CF3 | F |
| 26 | F | H | H | H | CN | H | F | F | F |
| 27 | F | H | H | H | CN | H | F | CF3 | F |

TABLE 25

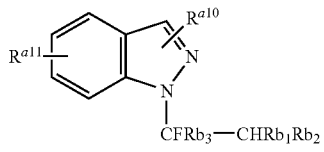

Indazole

| Compound No. | $R^{a11}$ | | | $R^{a10}$ | Rb1 | Rb2 | Rb3 |
|---|---|---|---|---|---|---|---|
| C1-12-1 | H | H | H | H | H | F | F | F |
| 2 | H | H | H | H | H | F | CF3 | F |
| 3 | H | H | H | H | H | H | H | F |
| 4 | H | H | H | H | H | CF3 | CF3 | F |
| 5 | H | H | H | H | H | CF3 | CF3 | OCH3 |
| 6 | F | H | H | H | H | F | F | F |
| 7 | F | H | H | H | H | F | CF3 | F |
| 8 | F | H | H | H | CH3 | F | F | F |
| 9 | F | H | H | H | CH3 | F | CF3 | F |
| 10 | H | H | H | H | CH3 | F | F | F |
| 11 | F | H | H | H | CH3 | F | CF3 | F |
| 12 | COOR | H | H | H | H | F | F | F |
| 13 | COOR | H | H | H | H | F | CF3 | F |
| 14 | CH3 | H | H | H | H | F | F | F |
| 15 | CH3 | H | H | H | H | F | CF3 | F |
| 16 | Ph | H | H | H | H | F | F | F |
| 17 | Ph | H | H | H | H | F | CF3 | F |
| 18 | H | H | H | H | COOR | F | F | F |
| 19 | H | H | H | H | COOR | F | CF3 | F |
| 20 | F | H | H | H | COOR | F | F | F |
| 21 | F | H | H | H | COOR | F | CF3 | F |
| 22 | H | H | H | H | CN | F | F | F |
| 23 | H | H | H | H | CN | F | CF3 | F |
| 24 | F | H | H | H | CN | F | F | F |
| 25 | F | H | H | H | CN | F | CF3 | F |

TABLE 26

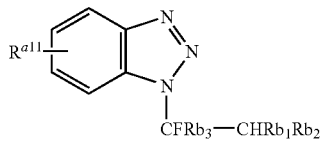

Benzotriazole

| Compound No. | $R^{a11}$ | | | Rb1 | Rb2 | Rb3 |
|---|---|---|---|---|---|---|
| C1-13-1 | H | H | H | H | F | F | F |
| 2 | H | H | H | H | F | CF3 | F |
| 3 | H | H | H | H | H | H | F |
| 4 | H | H | H | H | CF3 | CF3 | F |
| 5 | H | H | H | H | CF3 | CF3 | OCH3 |
| 6 | F | H | H | H | F | F | F |
| 7 | F | H | H | H | F | CF3 | F |
| 8 | F | F | H | H | F | F | F |
| 9 | F | F | H | H | F | CF3 | F |
| 10 | COOR | H | H | H | F | F | F |
| 11 | COOR | H | H | H | F | CF3 | F |
| 12 | CH3 | H | H | H | F | F | F |
| 13 | CH3 | H | H | H | F | CF3 | F |
| 14 | Ph | H | H | H | F | F | F |
| 15 | Ph | H | H | H | F | CF3 | F |
| 16 | OR | H | H | H | F | F | F |
| 17 | OR | H | H | H | F | CF3 | F |

Among these compounds, the following novel compounds which are not disclosed in prior art documents are especially preferable from the viewpoint of easy synthesis and availability.

Fluorine-containing imidazole compounds represented by the structural formula (C-1):

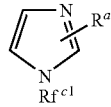

wherein $R^a$s are the same or different, and each is halogen atom, a functional group or an organic group and may be present or may not be present, and when $R^a$s are present, the whole or a part of hydrogen atoms of the heteroaromatic ring are substituted by them; $Rf^{c1}$ is the same as the formula (c) or is a monovalent organic group which may have at least one residue defined by deleting $Rf^{c1}$ group from the formula (C-1); $Rf^{c1}$ is not —CFHCF$_3$, —CF$_2$CFZ$^1$H and —CF=CFZ$^1$ (Z$^1$ is F or Cl).

$R^a$s are the same or different, and each is preferably H, F, Cl, —CH$_3$, —C$_2$H$_5$, —C$_3$H$_7$, —C$_4$H$_9$, —COOR, —CN, -Ph (phenyl group), —CH$_2$CN, —CH$_2$COOR, —CH$_2$SR, —CH$_2$CH(NR$_2$)COOR, —(CF)$_n$F, —(CF)$_n$H, —CF$_2$CF(CF$_3$)H or —(CF$_2$CH$_2$)$_n$H (Rs are the same or different, and each is a hydrocarbon group having 1 to 10 carbon atoms; n is an integer of 1 to 10,000).

Preferable example of $Rf^{c1}$ is one represented by the formula (c-1):

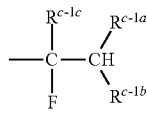

wherein $R^{c-1a}$ and $R^{c-1b}$ are the same or different, and each is F, —(CF$_2$)$_q$F, —O(CF$_2$)$_q$F, —CF(CF$_3$)$_2$, —(OCF$_2$CF(CF$_3$))$_p$—O(CF$_2$)$_q$F, —(OCF$_2$CF(CF$_3$))$_p$—OCF$_2$CF$_2$CF=CH$_2$, —(OCF$_2$CF(CF$_3$))$_p$—OCF$_2$CF$_2$CF$_2$CH$_2$I, —(OCF$_2$CF(CF$_3$))$_p$—O(CF$_2$)$_q$CFClCF$_2$Cl, —(OCF$_2$CF(CF$_3$))$_p$—O(CF$_2$)$_q$CF$_2$I, —(CF$_2$)$_q$—(OCF(CF$_3$)CF$_2$)$_p$OCF(CF$_3$)COOR, —(CF$_2$)$_q$—(OCF(CF$_3$)CF$_2$)$_p$OCF(CF$_3$)CH$_2$OR, —(CF$_2$CF$_2$)$_l$—(CF$_2$CF(CF$_3$))$_m$—(CF$_2$CH$_2$)$_n$-A, —(OCF$_2$CF(CF$_3$))$_x$—(OCF$_2$CF$_2$)$_y$—(OCF$_2$CF$_2$CF$_2$)$_z$—(OCF$_2$CF$_2$CH$_2$)$_w$-A, —CF$_2$CHFOCF$_2$CF$_2$CF=CF$_2$—B or —CF$_2$CH$_2$—(CF$_2$)$_r$—CH$_2$CF$_2$—B (Rs are the same or different, and each is a monovalent hydrocarbon group having 1 to 10 carbon atoms; A is H, F or a polymer end group; B is a residue defined by deleting $Rf^{c1}$ group from the formula (C-1); q is independently an integer of 1 to 9 in each formula; p is independently 0 or an integer of 1 to 20 in each formula; r is an integer of 1 to 10,000; each of l, m and n is independently 0 or an integer of 1 to 5,000, and the sum of l, m and n is an integer of 10 to 10,000; each of w, x, y and z is independently 0 or an integer of 1 to 30, and the sum of w, x, y and z is an integer of 3 to 60; $R^{c-1c}$ is F, H, —CF$_3$, —CF(CF$_3$)$_2$ or —CF$_2$CF(CF$_3$)$_2$; $R^{c-1a}$, $R^{c-1b}$ and $R^{c-1c}$ are not F at the same time.

Fluorine-containing pyrrole compounds represented by the structural formula (C-2):

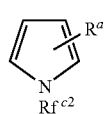

wherein $R^a$s are the same or different, and each is halogen atom, a functional group or an organic group and may be present or may not be present, and when $R^a$s are present, the whole or a part of hydrogen atoms of the heteroaromatic ring are substituted by them; $Rf^{c2}$ is the same as the formula (c) or is a monovalent organic group which may have at least one residue defined by deleting $Rf^{c2}$ group from the formula (C-2); $Rf^{c2}$ is not —$CFHCF_3$, —$CF_2CZ^1Z^2H$ and —$CF=CFZ^1$ ($Z^1$ is F or Cl; $Z^2$ is H, F, Cl, an alkyl group, a fluorinated alkyl group or a chlorinated alkyl group).

Preferable examples of $R^a$ and $Rf^{c2}$ are the same as $R^a$ and $Rf^{c1}$, respectively of the structural formula (C-1).

Fluorine-containing pyrazole compounds represented by the structural formula (C-3):

wherein $R^a$s are the same or different, and each is halogen atom, a functional group or an organic group and may be present or may not be present, and when $R^a$s are present, the whole or a part of hydrogen atoms of the heteroaromatic ring are substituted by them; $Rf^{c3}$ is the same as the formula (c) or is a monovalent organic group which may have at least one residue defined by deleting $Rf^{c3}$ group from the formula (C-3); $Rf^{c3}$ is not —$CFHCF_3$, —$CF_2CFZ^1H$ and —$CF=CFZ^1$ ($Z^1$ is F or Cl).

Preferable examples of $R^a$ and $Rf^{c3}$ are the same as $R^a$ and $Rf^{c1}$, respectively of the structural formula (C-1).

Fluorine-containing triazole compounds represented by the structural formula (C-4):

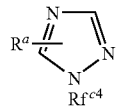

wherein $R^a$s are the same or different, and each is halogen atom, a functional group or an organic group and may be present or may not be present, and when $R^a$s are present, the whole or a part of hydrogen atoms of the heteroaromatic ring are substituted by them; $Rf^{c4}$ is the same as the formula (c) or is a monovalent organic group which may have at least one residue defined by deleting $Rf^{c4}$ group from the formula (C-4); $Rf^{c4}$ is not —$CFHCF_3$, —$CF_2CFZ^1H$ and —$CF=CFZ^1$ ($Z^1$ is F or Cl).

Preferable examples of $R^a$ and $Rf^{c4}$ are the same as $R^a$ and $Rf^{c1}$, respectively of the structural formula (C-1).

Fluorine-containing indole compounds represented by the structural formula (C-5):

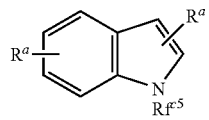

wherein $R^a$s are the same or different, and each is halogen atom, a functional group or an organic group and may be present or may not be present, and when $R^a$s are present, the whole or a part of hydrogen atoms of the heteroaromatic ring and/or the aromatic ring are substituted by them; $Rf^{c5}$ is the same as the formula (c) or is a monovalent organic group which may have at least one residue defined by deleting $Rf^{c5}$ group from the formula (C-5); $Rf^{c5}$ is not —$CFHCF_3$, —$CF_2CZ^1Z^2H$ and —$CF=CFZ^1$ ($Z^1$ is F or Cl; $Z^2$ is H, F, Cl, an alkyl group, a fluorinated alkyl group or a chlorinated alkyl group).

Preferable examples of $R^a$ and $Rf^{c5}$ are the same as $R^a$ and $Rf^{c1}$, respectively of the structural formula (C-1).

Fluorine-containing purine compounds represented by the structural formula (C-6):

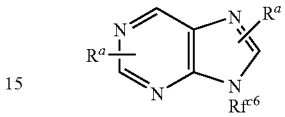

wherein each of $R^a$ is halogen atom, a functional group or an organic group and may be present or may not be present, and when $R^a$s are present, the whole or a part of hydrogen atoms of the heteroaromatic ring and/or the aromatic ring are substituted by them; $Rf^{c6}$ is the same as the formula (c) or is a monovalent organic group which may have at least one residue defined by deleting $Rf^{c6}$ group from the formula (C-6); $Rf^{c6}$ is not —$CFHCF_3$, —$CF_2CFZ^1H$ and —$CF=CFZ^1$ ($Z^1$ is F or Cl).

Preferable examples of $R^a$ and $Rf^{c6}$ are the same as $R^a$ and $Rf^{c1}$, respectively of the structural formula (C-1).

Fluorine-containing purine derivatives represented by the structural formula (C-7):

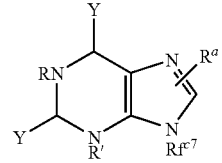

wherein $R^a$ is halogen atom, a functional group or an organic group and may be present or may not be present; Ys are the same or different and each is =O, —NRR', —OR, F or $F_2$; R and R' are the same or different and each is hydrogen atom, an alkyl group, an arylalkyl group, an organosilicon group, an alkoxyl group or a carboxyester group; $Rf^{c7}$ is the same as the formula (c) or is a monovalent organic group which may have at least one residue defined by deleting $Rf^{c7}$ group from the formula (C-7); $Rf^{c7}$ is not —$CFHCF_3$, —$CF_2CFZ^1H$ and —$CF=CFZ^1$ ($Z^1$ is F or Cl).

Preferable examples of $R^a$ and $Rf^{c7}$ are the same as $R^a$ and $Rf^{c1}$, respectively of the structural formula (C-1).

In those heteroaromatic ring compounds (C1) which are novel compounds, preferable examples of $Rf^{c1}$ to $Rf^{c7}$ in the fluoroalkyl group represented by the formula (c) are those having at least one kind of the units represented by the formulas (b-1) to (b-5) as $Rb^1$ to $Rb^3$ of the fluoroalkene (B) and/or those having the polymerizable group (b-6) at the end of at least one of $R^{b1}$ to $R^{b3}$. Preferable example of the polymerizable group is a carbon-carbon double bond.

Among the above-mentioned heteroaromatic ring compounds (C1) which are novel compounds, those having $CF_3$ group or oxygen atom as the Rf group are preferable as a starting material functioning to lower crystallinity and provide an ionic liquid having a low melting point. Especially preferable are Rf groups having two or more $CF_3$ groups or two or more oxygen atoms.

The second preparation process of the present invention is the process for preparing the salt (E) having an heteroaromatic ring structure having a N—Rf group in its ring, which is characterized in that a salt forming compound (D) is acted on the heteroaromatic ring compound (C) having a N—Rf group in its ring and obtained by the above-mentioned first preparation process, and if necessary, anion exchanging is carried out.

Examples of the salt forming compound (D) are, for instance, acids or alkylating agents represented by the formula (D1): Rd—$X^1$.

In the case of acids (Rd=H), inorganic acids such as HF, HCl, HBr, HI, $HClO_4$, $HNO_3$, $H_2CO_3$, $H_2SO_4$, $HBF_4$, $HPF_6$, $HSbF_6$, $HAlCl_4$, $HAlF_4$, $HAsF_6$ and $HSO_3F$, and organic acids such as R—$SO_3H$, R—COOH and R—$PO_3H$ can be used.

In addition, in the case of alkylating agents (Rd is an alkyl group), there are compounds having $X^1$ of F, Cl, Br, I, —$OSO_2R$, —OCOR, —OCOR or —$OPO_3R$ (R is a monovalent hydrocarbon group).

Examples of Rd are, for instance, hydrogen atom; linear or branched alkyl groups having 1 to 10 carbon atoms such as $CH_3$, $C_2H_5$, n-$C_3H_7$, i-$C_3H_7$ and $C_4H_9$; linear or branched fluoroalkyl groups having a unit such as $CF_3$, $C_2F_5$, n-$C_3F_7$, i-$C_3F_7$, $C_4F_9$, $CF_2CF_2Cl$, $CF_2CF_2Br$, $CF_2CF_2I$, $CH_2CF_3$, ($CF_2CF_2$)$_v$H (v is an integer of 1 to 5), $CF_2CHFCF_3$, $CF_2CH_3$, $CF_2CFClH$, $CF_2CH(CF_3)_2$, $CF_3CH_2CH_2$, $C_2F_5CH_2CH_2$, n-$C_3F_7CH_2CH_2$, i-$C_3F_7CH_2CH_2$, $C_4F_9CH_2CH_2$, —$CH_2CH_2C_2F_4CH_2CH_2$—, —$CH_2CH_2C_4F_8CH_2CH_2$— or —$CH_2CH_2C_6F_{12}CH_2CH_2$—; linear or branched hydroxyalkyl groups which may have fluorine and has a unit such as —($CF_2$)$_v$$CH_2$—OR (v is 0 or an integer of 1 to 10; R is hydrogen atom or an alkyl group which may be substituted by hydrogen atom or halogen atom), —$CH_2(CF_2CF_2)_v$$CH_2$—OR (v is an integer of 1 to 5; R is hydrogen atom or an alkyl group which may be substituted by hydrogen atom or halogen atom), —$CH_2CH_2(CF_2CF_2)_v$$CH_2$—OR (v is an integer of 1 to 5; R is hydrogen atom or an alkyl group which may be substituted by hydrogen atom or halogen atom), —$CH_2CH_2$($CF_2CF_2$)$_v$$CH_2CH_2$—OR (v is an integer of 1 to 5; R is hydrogen atom or an alkyl group which may be substituted by hydrogen atom or halogen atom) or —$CH_2(CF_2CF_2)_v$$CH_2CH_2$—OR (v is an integer of 1 to 5; R is hydrogen atom or an alkyl group which may be substituted by hydrogen atom or halogen atom).

With respect to the reaction conditions for allowing the salt forming compound (D) to act on the heteroaromatic ring compound, there can be employed usual conditions for salt forming reaction or alkylation reaction which are described in, for example, Y. L. Yagupolskii et al., J. Fluorine Chem., 126, pp. 669-672 (2005), C. E. Song et al., Chem. Comm., p. 1695 (2000), R. Hagiwara et al., J. Fluorine Chem., 99, p. 1 (1999), A. E. Visser et al., Green Chem., 2, p. 1 (2000) and M. Yoshizawa et al., Electrochem. Solid-State Lett., 4, E25 (2001).

For example, in the case where an acid is used as the salt forming compound (D), it is preferable to carry out the reaction at a reaction temperature of −30° C. to 150° C. in the absence of a solvent or by using a solvent such as diethyl ether, t-butyl methyl ether, diisopropyl ether, dibutyl ether, tetrahydrofuran, dioxane, dimethoxyethane, diglyme, triglyme, tetraglyme, ethyl acetate, methyl acetate, propyl acetate, butyl acetate, dimethyl sulfoxide, sulfolane, benzene, toluene, xylene, chloroform, methylene chloride, dichloroethane, trichloroethane, dichloropentafluoropropane, dichlorofluoroethane, trichlorotrifluoroethane, tetrachlorohexafluorobutane, dichlorooctafluorobutane, pentachloropentafluorohexane, dibromotetrafluoroethane, perfluorohexane, perfluoro(butyl tetrahydrofuran) or perfluorotributylamine, though it depends on kind of the fluorine-containing heteroaromatic ring compound (C) (salt forming method 1).

In addition, in the case where an alkylating agent is used as the salt forming compound (D), it is preferable to carry out the reaction at a reaction temperature of −30° C. to 150° C. in the absence of a solvent or by using a solvent such as diethyl ether, t-butyl methyl ether, diisopropyl ether, dibutyl ether, tetrahydrofuran, dioxane, dimethoxymethane, dimethoxyethane, diglyme, triglyme, tetraglyme, N,N-dimethylformamide, N,N-dimethylacetamide, N-methylpyrrolidone, ethyl acetate, methyl acetate, propyl acetate, butyl acetate, dimethyl sulfoxide, sulfolane, hexamethylphosphoric triamide, benzene, toluene, xylene, chloroform, methylene chloride, dichloroethane, trichloroethane, dichloropentafluoropropane, dichlorofluoroethane, trichlorotrifluoroethane, tetrachlorohexafluorobutane, dichlorooctafluorobutane, pentachloropentafluorohexane, dibromotetrafluoroethane, perfluorohexane, perfluoro(butyl tetrahydrofuran) or perfluorotributylamine, though it depends on kind of the fluorine-containing heteroaromatic ring compound (C) (salt forming method 2).

When the fluorine-containing heteroaromatic ring compound (C) is a compound having an imidazole skeleton, for example, the fluorine-containing imidazole compound (C1-1) or the fluorine-containing benzimidazole compound, the fluorine-containing purine compound (C-6) or the fluorine-containing purine derivative (C-7), the above-mentioned salt forming reaction proceeds especially satisfactorily, and Rd is bonded to nitrogen atom other than N—Rf of the fluorine-containing heteroaromatic ring to give a cation and $X^1$ becomes a counter anion.

Further, the counter anion can be changed to various anions, if necessary, by anion exchange of the counter anion of the salt of fluorine-containing heteroaromatic ring compound obtained by allowing such a salt forming compound (D) to act on the heteroaromatic ring compound.

Examples of a compound usable for the anion exchange are, for instance, M-$ClO_4$, M-$NO_3$, $M_2$-$SO_4$, $M_2$-$CO_3$, M-$BF_4$, M-$BCl_4$, M-$PF_6$, M-$SbF_6$, M-$AlCl_4$, M-$Al_2Cl_7$, M-$AlF_4$, M-$AsF_6$, M-N(CN)$_2$, M-F, a mixture of M-F and HF, M-N($SO_2R$)($SO_2R'$), M-$OSO_2R$, M-OCOR, M-$OPO_3R$, M-C($SO_2R$)$_2$($SO_2R'$) and M-[RCOCHCOR'], wherein R and R' are the same or different and each is —($CF_2$)$_n$F (n=1 to 20), —CF($CF_3$)OCF$_3$, —CF($CF_3$)—[OCF$_2$CF($CF_3$)]$_n$—O ($CF_2$)$_m$—F, —CF($CF_3$)—[OCF$_2$CF($CF_3$)]$_n$—O($CF_2$)$_m$—CFClCF$_2$Cl, —CF($CF_3$)—[OCF$_2$CF($CF_3$)]$_n$—O($CF_2$)$_m$—$CF_2I$, —CF($CF_3$)—[OCF$_2$CF($CF_3$)]$_n$—OCF$_2$CF$_2$CF=CH$_2$, —CF($CF_3$)—[OCF$_2$CF($CF_3$)]$_n$—OCF$_2$CF$_2$CF$_2$CH$_2$I, —CF($CF_3$)—[OCF$_2$CF($CF_3$)]$_n$—OCF$_2$CF$_2$SO$_2$X, —($CF_2$)$_m$—[OCF($CF_3$)$CF_2$]$_n$OCF($CF_3$)COOX, —($CF_2$)$_m$—[OCF($CF_3$)$CF_2$]$_n$OCF($CF_3$)CH$_2$OX, —($CF_2CF_2$)$_p$—($CF_2$CF($CF_3$))$_q$—($CF_2CH_2$)$_r$—($CF_2$CFCl)$_s$-A, or —(OCF$_2$CF($CF_3$))$_x$—(OCF$_2$CF$_2$)$_y$—(OCF$_2$CF$_2$CF$_2$)$_z$—(OCF$_2$CF$_2$CH$_2$)$_w$—(OCF$_2$)$_v$-A (in these formulas, A represents H, F, an end group of a polymerization initiator or a modified group thereof; n and m are the same or different and each is 0 or an integer of 1 to 10; each of p, q, r and s is independently 0 or an integer of 1 to 5,000, and the sum of p, q, r and s is an integer of 10 to 10,000; each of x, y, z, v and w is independently 0 or an integer of 1 to 60, and the sum of x, y, z, w and v is an integer of 3 to 60); M is Li, Na, K, Rb, Cs, ½Mg, ⅓Al, Ag, ½Zn, ½Ni, ⅓Fe, H or $NH_4$.

In addition, the compound may be a polymer chain containing 1 to 100% by mass of a polymer unit represented by:

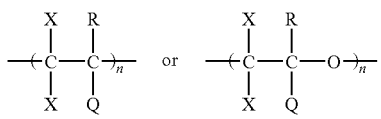

wherein X is H or F; R is H, F, $CH_3$ or $CF_3$; Q is $-Q^{1-}$, $—[OCF_2CF(CF_3)]_{0-10}O(CF_2)_{0-8}-Q^{1-}$, $—(CF_2)_{0-8}[OCF(CF_3)CF_2]_{0-10}OCF(CF_3)-Q^{1-}$, $(CH_3)_{0-8}(CF_2)_{0-20}(CH_3)_{0-8}-Q^{1-}$ or $—(C_6H_4)(CH_3)_{0-8}-Q^{1-}$ ($Q^{1-}$s are the same or different and each is $COO^-$ or $SO^{3-}$). It is desirable that a number average molecular weight of the polymer chain is about $1 \times 10^3$ to about $8 \times 10^5$, from the viewpoint of solubility of the polymer in a solvent.

A copolymerizable comonomer is not limited particularly, and may be optionally selected depending on characteristics intended to be imparted. Nonlimiting examples of preferable comonomers are, for instance, $CF_2=CF_2$, $CF_2=CF(CF_3)$, $CF_2=CFCl$, $CF_2=CH_2$, $CF_2=CFH$, perfluoro(butenyl vinyl ether), perfluoro-2,2-dimethyldioxole, perfluorodioxole, $CH_2=CH_2$, $CH_2=CH(CH_3)$, $CH_2=CHCH=CH_2$, $CH_2=CHCl$, $CH_2=CCl_2$, $CH_2=CHCO_2R$ (R is hydrogen atom or an alkyl group which may be substituted by hydrogen atom or halogen atom), $CH_2=C(CH_3)CO_2R$ (R is hydrogen atom or an alkyl group which may be substituted by hydrogen atom or halogen atom), $CH_2=CFCO_2R$ (R is hydrogen atom or an alkyl group which may be substituted by hydrogen atom or halogen atom), $CH_2=C(CF_3)CO_2R$ (R is hydrogen atom or an alkyl group which may be substituted by hydrogen atom or halogen atom), $CH_2=CHC_6X_5$ (X is H or F), $CH_2=C(CH_3)C_6X_5$ (X is H or F), $CH_2=CFC_6X_5$ (X is H or F), $CH_2=C(CF_3)C_6X_5$ (X is H or F), $CH_2=CHCN$, $CH_2=C(CH_3)CN$, $CH_2=CFCN$, $CH_2=C(CF_3)CN$, $CH_2=CHOCO_2R$ (R is an alkyl group which may be substituted by hydrogen atom or halogen atom), $CH_2=CHOR$ (R is an alkyl group which may be substituted by hydrogen atom or halogen atom), $CH_2=CFCF_2CF_2CF_2O[CF(CF_3)CF_2]_nOCF(CF_3)COOR$ (n is 0 or an integer of 1 to 20; R is hydrogen atom or an alkyl group which may be substituted by hydrogen atom or halogen atom), $CH_2=CFCF_2CF_2O[CF(CF_3)CF_2]_nOCF(CF_3)CH_2OR$ (n is 0 or an integer of 1 to 20; R is hydrogen atom or an alkyl group which may be substituted by hydrogen atom or halogen atom), $CH_2=CFCF_2CF_2O[CF(CF_3)CF_2]_nOCFCF_3$ (n is 0 or an integer of 1 to 20), sulfur dioxide, ethylene oxide, propylene oxide, tetrafluoroethylene oxide, hexafluoropropylene oxide, fluorophosgene and hexafluoroacetone.

Examples of the salt (E) of fluorine-containing heteroaromatic ring compound so-obtained by acting the salt forming compound (D) and if necessary, conducting anion exchange are, for instance, a salt of heteroaromatic ring compound represented by the formula (E1):

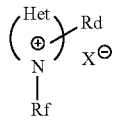

wherein

is a moiety forming a heteroaromatic ring together with a nitrogen atom and the whole or a part of its hydrogen atoms may be substituted by the same or different organic groups; Rf is $Rf^e$ where $Rf^e$ is the same as the formula (c) or is a monovalent organic group which may have at least one residue defined by deleting Rf group from the formula (E1); Rd is H or a monovalent organic group; X is a counter anion.

Examples of the salt (E) represented by the formula (E1) are fluoride, chloride, bromide, iodide, perchlorate, nitrate, sulfate, carbonate, tetrafluoroborate, hexafluorophosphate, hexafluoroantimonate, tetrachloroaluminate, tetrafluoroaluminate, hexafluoroarsenate, fluorosulfonate, dicyanamide salt, $F(HF)_n$ salt (n=1 to 10), bisperfluoro(C1 to C20)alkylsulfonylamide salt (two alkyl groups are the same or different), perfluoro(C1 to C20)alkylsulfonate, perfluoro(C1 to C20)alkylcarboxylate, perfluoro(C1 to C20)alkylphosphonate, trisperfluoro(C1 to C20)alkylsulfonyl carbonate (three alkyl groups are the same or different), 1-perfluoroalkyl-3-perfluoro(C1 to C10) alkyl-1,3-diketonate (two alkyl groups are the same or different), dichlorocuprate, tetrachloroborate, heptachlorodialuminate and trichlorozincate of the fluorine-containing heteroaromatic ring compound (C).

Especially the salt of fluorine-containing imidazole compound represented by the structural formula (E-1):

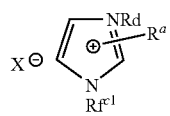

wherein $R^a$s are the same or different, and each is halogen atom, a functional group or an organic group and may be present or may not be present, and when $R^a$s are present, the whole or a part of hydrogen atoms of the heteroaromatic ring are substituted by them; $Rf^{e1}$ is the same as the formula (c) or is a monovalent organic group which may have at least one residue defined by deleting $Rf^{e1}$ group from the formula (C-1); $Rf^{e1}$ is not $—CF_2CF_2H$, $—CF=CF_2$, $—CF_2CFClH$, $—CF_2=CFCl$ and $—CFHCF_3$; Rd is H or a monovalent organic group; X is a counter anion, is a novel compound.

In the formula (E-1), preferable examples of $R^a$, $Rf^{e1}$, Rd and X are those raised supra. $Rf^{e1}$ is preferably one having the perfluoroalkylene group of the formula (b-4) having a branched chain and/or the fluoroether unit of the formula (b-5), especially preferably one which has the perfluoroalkylene group of the formula (b-4) having a branched chain and two or more $CF_3$ groups or two or more oxygen atoms and/or the fluoroether unit of the formula (b-5) since a liquid state is easily exhibited at room temperature.

In addition, the end of at least one of $R^a$ and $Rf^{e1}$ may be the polymerizable group (b-6). Examples of the polymerizable group are, for instance, a carbon-carbon double bond, a hydroxyl group, a carboxyl group, an amino group, an isocyanate group, a thiol group and a thioisocyanate group, and especially preferable is a carbon-carbon double bond.

The heteroaromatic ring compound (C) having a N—Rf group in its ring which is prepared by the first preparation process of the present invention not only is useful as a starting material for the second preparation process but also can be expected as various materials comprising a heteroaromatic ring compound having a stable N—Rf group in the ring thereof, for example, curing agents such as an epoxy resin and a polyurethane resin, various agricultural chemicals, intermediates for medicines such as antibiotics and anti-AIDS drugs and intermediates of dyes.

The salt (E) of heteroaromatic ring compound having a N—Rf group in its ring which is prepared by the second preparation process of the present invention can be used as various materials comprising a heteroaromatic ring compound having a stable N—Rf group in the rings thereof, for example, ionic liquids having various functions useful for electrolytes for fuel cell, secondary battery, capacitor, dye-sensitized solar cell and electrochromic device, and reaction media, catalysis, and chemical separation and reprocessing of nuclear fuel, and in addition, can be expected to be curing agents such as an epoxy resin and a polyurethane resin, various agricultural chemicals, intermediates for medicines such as antibiotics and anti-AIDS drugs and intermediates of dyes.

It is known that usually when a hydrocarbon ionic liquid is mixed to a perfluoro solvent, it is separated and are not mixed to each other, and an ionic liquid having a fluoroalkyl chain has an effect of dispersing a hydrocarbon ionic liquid in a perfluoro solvent (T. L. Merrigan et al., Chem. Comm., pp. 2051-2052 (2000)), and it is also known that when a hydrocarbon ionic liquid is mixed to Nafion (trade mark of Du Pont) which is a fluorine-containing resin having a sulfonic acid group, cation exchange occurs and there is an effect that properties as an electrolyte rather than properties as a solvent are exhibited (T. Schafer, et al., Chem. Comm., pp. 2594-2096 (2005). In such applications, it can be considered that when an ionic liquid having a fluoroalkyl chain is used for resins having a high content of fluorine atoms, cation exchange can be carried out more effectively.

Therefore, even if the salt (E) of heteroaromatic ring compound having a N—Rf group in its ring is a solid at normal temperature, as described in the above-mentioned publications, by dispersing or dissolving the salt (E) of heteroaromatic ring compound having a N—Rf group in its ring in a polymer, a solvent or an ionic liquid, ionic conductivity and a function of accelerating dispersion of additives can be exhibited by participation of a structure of N—Rf group.

EXAMPLES

The present invention is then explained by means of examples, but is not limited thereto.

Measuring methods used in the present invention are as follows.

(Method of Identification of Compound)

Compounds are identified by $^1$H-NMR analysis, $^{19}$F-NMR analysis, IR analysis and elementary analysis.

NMR measuring equipment: available from BRUKER
$^1$H-NMR measuring condition: 300 MHz (tetramethylsilane=0 ppm)
$^{19}$F-NMR measuring condition: 282 MHz (trichlorofluoromethane=0 ppm)
IR analysis: Measurement is carried out at room temperature with a Fourier-transform infrared spectrophotometer 1760X available from Perkin Elmer Co., Ltd.

Example 1

Into a 50 ml autoclave was poured 6.81 g of imidazole (100 mmol, melting point: 89° C.), and evacuation and replacement of atmosphere in the autoclave with nitrogen gas were carried out three times. After the inside of a system was evacuated, tetrafluoroethylene (TFE) was introduced until the inside pressure of the system reached 0.1 MPa·G. Then the temperature of the reaction system was increased to 100° C. which was higher than the melting point of imidazole, and TFE was further introduced to maintain the inside pressure of the reaction system at 0.3 to 0.5 MPa·G. Supply of TFE was stopped when the amount of TFE reached 1.1 equivalents (11 g=110 mmol) to imidazole, and stirring was continued at 100° C. Eight hours after starting of the stirring, the inside of the reaction system was brought to room temperature, followed by evacuation and then distillation in such a state to obtain 14.5 g of distillate at 93° C./96 mmHg (yield: 86%).

According to a NMR analysis, it was confirmed that this product was 1-(1,1,2,2-tetrafluoroethyl)imidazole. To this crude reaction product was added ethyl trifluoroacetate (2.84 g=20 mmol), and yield by a $^{19}$F-NMR analysis based on ethyl trifluoroacetate was 98%.

$^{19}$F-NMR (CD$_3$COCD$_3$): δ−102.3 (2F), −142.3 (2F) ppm
$^1$H-NMR (CD$_3$COCD$_3$): δ6.82 (1H, tt), 7.18 (1H, s), 7.48 (1H, s), 8.04 (1H, s) ppm Example 2

Into a 50 ml autoclave were poured 1.36 g (20 mmol) of imidazole and tetrahydrofuran (30 ml), and the inside of the autoclave was cooled to −78° C., and evacuation and replacement of atmosphere in the autoclave with nitrogen gas were carried out three times. After the inside of a system was evacuated, TFE was introduced until the inside pressure of the system reached 0.1 MPa·G. Then the temperature of the reaction system was increased to 100° C. which was higher than the melting point of imidazole, and TFE was further introduced to maintain the inside pressure of the reaction system at 0.3 to 0.5 MPa·G. Supply of TFE was stopped when the amount of TFE reached 1.1 equivalents (2.2 g=22 mmol) to imidazole, and stirring was continued at 100° C. Fifteen hours after starting of the stirring, the inside of the reaction system was brought to room temperature, followed by evacuation, and ethyl trifluoroacetate (1.42 g=10 mmol) was added to this crude reaction product. Yield by a $^{19}$F-NMR analysis based on ethyl trifluoroacetate was 89%.

Example 3

Into a 50 ml autoclave were poured 6.81 g (100 mmol) of imidazole and tetrahydrofuran (1.0 ml) as a melting point depressor, and the inside of the autoclave was cooled to −78° C., and evacuation and replacement of atmosphere in the autoclave with nitrogen gas were carried out three times. After the inside of a system was evacuated, TFE was introduced until the inside pressure of the system reached 0.1 MPa·G. Then the temperature of the reaction system was increased to 50° C., and TFE was further introduced to maintain the inside pressure of the reaction system at 0.3 to 0.5 MPa·G. Supply of TFE was stopped when the amount of TFE reached 1.1 equivalents (11 g=110 mmol) to imidazole, and stirring was continued at 50° C. Eight hours after starting of the stirring, the inside of the reaction system was brought to room temperature, followed by evacuation to terminate the reaction. To this crude reaction product was added 2.84 g (20 mmol) of ethyl trifluoroacetate, and yield by a $^{19}$F-NMR analysis based on ethyl trifluoroacetate was 92%.

Comparative Example 1

Into a 50 ml autoclave were poured 10.6 g (100 mmol) of potassium salt of imidazole and tetrahydrofuran (30 ml), and the inside of the autoclave was cooled to −78° C., and evacuation and replacement of atmosphere in the autoclave with nitrogen gas were carried out three times. After the inside of a system was evacuated, TFE was introduced until the inside pressure of the system reached 0.1 MPa·G. Then the temperature of the reaction system was increased to 100° C., and TFE was further introduced to maintain the inside pressure of the reaction system at 0.3 to 0.5 MPa·G. Supply of TFE was stopped when the amount of TFE reached 1.1 equivalents (11 g=110 mmol) to the potassium salt of imidazole, and stirring was continued at 100° C. Fifteen hours after starting of the stirring, the inside of the reaction system was brought to room temperature, followed by evacuation to terminate the reaction. To this crude reaction product was added 2.84 g (20 mmol) of ethyl trifluoroacetate, and it was confirmed by a $^{19}$F-NMR analysis based on ethyl trifluoroacetate that 1-(1,1,2,2-tetrafluoroethyl)imidazole had been produced at yield of 13% and 1-(1,2,2-trifluoroethenyl)imidazole had been produced at yield of 56%. Also according to gas chromatography analysis, it was confirmed that the remaining imidazole was 14%.

Then the entire crude reaction product was poured into water (30 ml), and subjected to extraction with ethyl acetate. After separation of an organic layer, drying was carried out with magnesium sulfate and concentration was conducted under reduced pressure. Then thereto was added 1.46 g (10 mmol) of benzotrifluoride, and it was confirmed by a $^{19}$F-NMR analysis based on benzotrifluoride that 1-(1,1,2,2-tetrafluoroethyl)imidazole had been produced at yield of 7% and 1-(1,2,2-trifluoroethenyl)imidazole had been produced at yield of 39%.

Comparative Example 2

Into a 50 ml autoclave were poured 0.20 g (5 mmol) of metallic potassium and tetrahydrofuran (10 ml), and the inside of the autoclave was cooled to –78° C., and evacuation and replacement of atmosphere in the autoclave with nitrogen gas were carried out three times. Then thereto was added a solution obtained by dissolving 1.36 g (20 mmol) of imidazole in tetrahydrofuran (10 ml) at 10° C. over 30 minutes under pressurized nitrogen atmosphere. Thereafter tetrafluoroethylene (TFE) was introduced until the inside pressure of the system reached 0.1 MPa·G. Then the temperature of the reaction system was increased to 100° C., and TFE was further introduced to maintain the inside pressure of the reaction system at 0.3 to 0.5 MPa·G. Supply of TFE was stopped when the amount of TFE reached 1.1 equivalents (2.2 g=22 mmol) to imidazole, and stirring was continued at 100° C. Eight hours after starting of the stirring, the inside of the reaction system was brought to room temperature, followed by evacuation to terminate the reaction. To this crude reaction product was added 1.42 g (10 mmol) of ethyl trifluoroacetate, and it was confirmed by a $^{19}$F-NMR analysis based on ethyl trifluoroacetate that 1-(1,1,2,2-tetrafluoroethyl)imidazole had been produced at yield of 55% and 1-(1,2,2-trifluoroethenyl)imidazole had been produced at yield of 23%. Also according to gas chromatography, it was confirmed that the remaining imidazole was 9%.

Then the entire crude reaction product was poured into water (30 ml), and subjected to extraction with ethyl acetate. After separation of an organic layer, drying was carried out with magnesium sulfate and concentration was conducted under reduced pressure. Then thereto was added 1.46 g (10 mmol) of benzotrifluoride, and it was confirmed by a $^{19}$F-NMR analysis based on benzotrifluoride that 1-(1,1,2,2-tetrafluoroethyl)imidazole had been produced at yield of 41% and 1-(1,2,2-trifluoroethenyl)imidazole had been produced at yield of 19%.

Example 4

Into a 50 ml autoclave was poured 6.81 g (100 mmol) of imidazole, and evacuation and replacement of atmosphere in the autoclave with nitrogen gas were carried out three times at room temperature. After the inside of a system was evacuated, hexafluoropropylene (HFP) was introduced until the inside pressure of the system reached 0.1 MPa·G. Then the temperature of the reaction system was increased to 100° C. which was higher than the melting point of imidazole, and HFP was further introduced to maintain the inside pressure of the reaction system at 0.3 to 0.5 MPa·G. Supply of HFP was stopped when the amount of HFP reached 1.1 equivalents (17 g=110 mmol) to imidazole, and stirring was continued at 100° C. Eight hours after starting of the stirring, the inside of the reaction system was brought to room temperature, followed by evacuation and then distillation in such a state to obtain 16.5 g of distillate at 93° C./53 mmHg (yield: 76%).

According to a NMR analysis, it was confirmed that this product was 1-(1,1,2,3,3,3-hexafluoropropyl)imidazole. To this crude reaction product was added 2.84 g (20 mmol) of ethyl trifluoroacetate, and yield by a $^{19}$F-NMR analysis based on ethyl trifluoroacetate was 83%.

$^{19}$F-NMR (CD$_3$COCD$_3$): δ–73.9 (3F), –84.4 (1F), –91.2 (1F), –210.0 (1F) ppm $^1$H-NMR (CD$_3$COCD$_3$): δ6.26 (1H, m), 7.18 (1H, s), 7.53 (1H, s), 8.09 (1H, s) ppm Example 5

Into a 50 ml autoclave was poured 6.71 g of pyrrole (100 mmol, melting point of –23° C.), and evacuation and replacement of atmosphere in the autoclave with nitrogen gas were carried out three times at room temperature. After the inside of a system was evacuated, hexafluoropropylene (HFP) was introduced until the inside pressure of the system reached 0.1 MPa·G. Then the temperature of the reaction system was increased to 60° C., and HFP was further introduced to maintain the inside pressure of the reaction system at 0.3 to 0.5 MPa·G. Supply of HFP was stopped when the amount of HFP reached 1.1 equivalents (17 g=110 mmol) to pyrrole, and stirring was continued at 100° C. Eight hours after starting of the stirring, the inside of the reaction system was brought to room temperature, followed by evacuation and then distillation in such a state to obtain 18.0 g of distillate at 108° C. (yield: 83%).

According to a NMR analysis, it was confirmed that this product was 1-(1,1,2,3,3,3-hexafluoropropyl)pyrrole. To this crude reaction product was added 2.84 g (20 mmol) of ethyl trifluoroacetate, and yield by a $^{19}$F-NMR analysis based on ethyl trifluoroacetate was 94%.

$^{19}$F-NMR (CD$_3$COCD$_3$): δ–74.2 (3F), –86.4 (1F), –89.5 (1F), –211.2 (1F) ppm $^1$H-NMR (CD$_3$COCD$_3$): δ6.26 (1H, m), 6.24 (2H, m), 6.75 (2H, m) ppm Example 6

Into a 50 ml autoclave was poured 6.81 g of pyrazole (100 mmol, melting point of 67° C.), and evacuation and replacement of atmosphere in the autoclave with nitrogen gas were carried out three times at room temperature. After the inside of a system was evacuated, hexafluoropropylene (HFP) was introduced until the inside pressure of the system reached 0.1 MPa·G. Then the temperature of the reaction system was increased to 75° C., and HFP was further introduced to maintain the inside pressure of the reaction system at 0.3 to 0.5 MPa·G. Supply of HFP was stopped when the amount of HFP reached 1.1 equivalents (17 g=110 mmol) to pyrazole, and stirring was continued at 100° C. Eight hours after starting of the stirring, the inside of the reaction system was brought to room temperature, followed by evacuation and then distillation in such a state to obtain 19.2 g of distillate at 88° C./96 mmHg (yield: 88%).

According to a NMR analysis, it was confirmed that this product was 1-(1,1,2,3,3,3-hexafluoropropyl)pyrazole. To this crude reaction product was added 2.84 g (20 mmol) of ethyl trifluoroacetate, and yield by a $^{19}$F-NMR analysis based on ethyl trifluoroacetate was 91%.

$^{19}$F-NMR (CD$_3$COCD$_3$): δ–75.5 (3F), –83.8 (1F), –90.0 (1F), –214.2 (1F) ppm $^1$-NMR (CD$_3$COCD$_3$): δ6.10 (1H, m), 6.26 (1H, m), 7.74 (2H, s) ppm Example 7

Into a 50 ml autoclave was poured 6.91 g of 1,2,4-triazole (100 mmol, melting point of 120° C.), and evacuation and replacement of atmosphere in the autoclave with nitrogen gas were carried out three times at room temperature. After the inside of a system was evacuated, hexafluoropropylene (HFP) was introduced until the inside pressure of the system reached 0.1 MPa·G. Then the temperature of the reaction system was increased to 135° C., and HFP was further introduced to maintain the inside pressure of the reaction system at 0.3 to 0.5 MPa·G. Supply of HFP was stopped when the amount of HFP reached 1.1 equivalents (17 g=110 mmol) to 1,2,4-triazole, and stirring was continued at 100° C. Eight hours after starting of the stirring, the inside of the reaction system was brought to room temperature, followed by evacuation and then distillation in such a state to obtain 17.5 g of distillate at 90° C./90 mmHg (yield: 80%).

According to a NMR analysis, it was confirmed that this product was 1-(1,1,2,3,3,3-hexafluoropropyl)-1,2,4-triazole. To this crude reaction product was added 2.84 g (20 mmol) of ethyl trifluoroacetate, and yield by a $^{19}$F-NMR analysis based on ethyl trifluoroacetate was 87%.

$^{19}$F-NMR (CD$_3$COCD$_3$): δ–72.6 (3F), –88.9 (1F), –93.4 (1F), –211.4 (1F) ppm $^1$H-NMR (CD$_3$COCD$_3$): δ6.25 (1H, m), 8.09 (1H, s), 8.38 (1H, s) ppm Example 8

Into a 50 ml autoclave were poured 8.21 g of 2-methylimidazole (100 mmol, melting point of 142° C.) and tetrahydrofuran (3.0 ml) as a melting point depressor, and evacuation and replacement of atmosphere in the autoclave with nitrogen gas were carried out three times at –78° C. After the inside of a system was evacuated, hexafluoropropylene (HFP) was introduced until the inside pressure of the system reached 0.1 MPa·G. Then the temperature of the reaction system was increased to 100° C., and HFP was further introduced to maintain the inside pressure of the reaction system at 0.3 to 0.5 MPa·G. Supply of HFP was stopped when the amount of HFP reached 1.1 equivalents (17 g=110 mmol) to 2-methylimidazole, and stirring was continued at 100° C. Eight hours after starting of the stirring, the inside of the reaction system was brought to room temperature, followed by evacuation and then distillation in such a state to obtain 20.1 g of distillate at 78° C./24 mmHg (yield: 86%).

According to a NMR analysis, it was confirmed that this product was 2-methyl-1-(1,1,2,3,3,3-hexafluoropropyl)imidazole. To this crude reaction product was added 2.84 g (20 mmol) of ethyl trifluoroacetate, and yield by a $^{19}$F-NMR analysis based on ethyl trifluoroacetate was 96%.

$^{19}$F-NMR (CD$_3$COCD$_3$): δ–73.9 (3F), –84.4 (1F), –91.2 (1F), –210.0 (1F) ppm $^1$H-NMR (CD$_3$COCD$_3$): δ2.65 (3H, s), 6.26 (1H, m), 7.15 (1H, s), 7.50 (1H, s) ppm Example 9

Into a 50 ml autoclave was poured 11.7 g of indole (100 mmol, melting point of 52° C.), and evacuation and replacement of atmosphere in the autoclave with nitrogen gas were carried out three times at room temperature. After the inside of a system was evacuated, tetrafluoroethylene (TFE) was introduced until the inside pressure of the system reached 0.1 MPa·G. Then the temperature of the reaction system was increased to 60° C., and TFE was further introduced to maintain the inside pressure of the reaction system at 0.3 to 0.5 MPa·G. Supply of TFE was stopped when the amount of TFE reached 1.1 equivalents (11 g=110 mmol) to indole, and stirring was continued at 60° C. Eight hours after starting of the stirring, the inside of the reaction system was brought to room temperature, followed by evacuation and then distillation in such a state to obtain 16.0 g of distillate at 77° C./8.0 mmHg (yield: 74%).

According to a NMR analysis, it was confirmed that this product was 1-(1,1,2,2-tetrafluoroethyl)indole. To this crude reaction product was added 2.84 g (20 mmol) of ethyl trifluoroacetate, and yield by a $^{19}$F-NMR analysis based on ethyl trifluoroacetate was 87%.

$^{19}$F-NMR (CD$_3$COCD$_3$): δ–98.1 (2F), –144.6 (2F) ppm $^1$H-NMR (CD$_3$COCD$_3$): δ6.23 (1H, m), 6.52 (1H, s), 7.00-7.30 (4H, m), 7.65 (1H, m) ppm Example 10

Into a 50 ml autoclave were poured 12.0 g of purine (100 mmol, melting point of 214° C.) and tetrahydrofuran (3.0 ml) as a melting point depressor, and the inside of the autoclave was cooled to –78° C., and evacuation and replacement of atmosphere in the autoclave with nitrogen gas were carried out three times. After the inside of a system was evacuated, tetrafluoroethylene (TFE) was introduced as a melting point depressor until the inside pressure of the system reached 0.1 MPa·G. Then the temperature of the reaction system was increased to 120° C., and TFE was further introduced to maintain the inside pressure of the reaction system at 0.3 to 0.5 MPa·G. Supply of TFE was stopped when the amount of TFE reached 1.1 equivalents (11 g=110 mmol) to purine, and stirring was continued at 120° C. Eight hours after starting of the stirring, the inside of the reaction system was brought to room temperature, followed by evacuation, dissolution in ethanol and re-crystallization with hexane to obtain 13.6 g of a solid (yield: 62%).

According to a NMR analysis, it was confirmed that this product was 1-(1,1,2,2-tetrafluoroethyl)purine. To this crude reaction product was added 2.84 g (20 mmol) of ethyl trifluoroacetate, and yield by a $^{19}$F-NMR analysis based on ethyl trifluoroacetate was 77%.

$^{19}$F-NMR (CD$_3$COCD$_3$): δ–93.6 (2F), –140.9 (2F) ppm $^1$H-NMR (CD$_3$COCD$_3$): δ7.25 (1H, s), 8.70 (1H, s), 9.00 (1H, s), 9.21 (1H, s) ppm Example 11

Into a 50 ml autoclave were poured 18.1 g of theophylline (100 mmol, melting point of 274° C.) which was a purine derivative, and tetrahydrofuran (5.0 ml) as a melting point depressor, and the inside of the autoclave was cooled to –78° C. and evacuation and replacement of atmosphere in the autoclave with nitrogen gas were carried out three times.

After the inside of a system was evacuated, tetrafluoroethylene (TFE) was introduced until the inside pressure of the system reached 0.1 MPa·G. Then the temperature of the reaction system was increased to 120° C., and TFE was further introduced to maintain the inside pressure of the reaction system at 0.3 to 0.5 MPa·G. Supply of TFE was stopped when the amount of TFE reached 1.1 equivalents (11 g=110 mmol) to theophylline, and stirring was continued at 120° C. Eight hours after starting of the stirring, the inside of the reaction system was brought to room temperature, followed by evacuation, dissolution in ethanol and re-crystallization with hexane to obtain 14.5 g of a solid (yield: 52%).

According to a NMR analysis, it was confirmed that this product was 1-(1,1,2,2-tetrafluoroethyl)theophylline. To this crude reaction product was added 2.84 g (20 mmol) of ethyl trifluoroacetate, and yield by a $^{19}$F-NMR analysis based on ethyl trifluoroacetate was 81%.

$^{19}$F-NMR (DMSO-$d_6$): δ−95.8 (2F), −140.1 (2F) ppm
$^1$H-NMR (DMSO-$d_6$): δ3.24 (3H, s), 3.44 (3H, s), 7.30 (1H, m), 7.98 (1H, s) ppm Example 12

Into a 50 ml autoclave was poured 21.2 g of N-(t-butoxycarbonyl)histamine (100 mmol, melting point of 83° C.) which was an imidazole compound, and the inside of the autoclave was cooled to −78° C. and evacuation and replacement of atmosphere in the autoclave with nitrogen gas were carried out three times. After the inside of a system was evacuated, tetrafluoroethylene (TFE) was introduced until the inside pressure of the system reached 0.1 MPa·G. Then the temperature of the reaction system was increased to 90° C., and TFE was further introduced to maintain the inside pressure of the reaction system at 0.3 to 0.5 MPa·G. Supply of TFE was stopped when the amount of TFE reached 1.1 equivalents (11 g=110 mmol) to N-(t-butoxycarbonyl)histamine, and stirring was continued at 90° C. Eight hours after starting of the stirring, the inside of the reaction system was brought to room temperature, followed by evacuation, dissolution in chloroform and re-crystallization with hexane to obtain 17.6 g of a solid (yield: 63%).

According to a NMR analysis, it was confirmed that this product was N-(t-butoxycarbonyl)-N$^1$-(1,1,2,2-tetrafluoroethyl)histamine. To this crude reaction product was added 2.84 g (20 mmol) of ethyl trifluoroacetate, and yield by a $^{19}$F-NMR analysis based on ethyl trifluoroacetate was 91%.

$^{19}$F-NMR (CD$_3$COCD$_3$): δ−100.4 (2F), −139.8 (2F) ppm
$^1$H-NMR (CD$_3$COCD$_3$): δ1.31 (9H, s), 2.70-3.10 (4H, m), 6.80 (1H, s), 7.27 (1H, m), 7.54 (1H, s) ppm Example 13

Into a 50 ml autoclave were poured 31.8 g (100 mmol) of Nα-(t-butoxycarbonyl)tryptophan methyl ester which was an indole compound, and tetrahydrofuran (5.0 ml) as a melting point depressor, and the inside of the autoclave was cooled to −78° C. and evacuation and replacement of atmosphere in the autoclave with nitrogen gas were carried out three times. After the inside of a system was evacuated, tetrafluoroethylene (TFE) was introduced until the inside pressure of the system reached 0.1 MPa·G. Then the temperature of the reaction system was increased to 120° C., and TFE was further introduced to maintain the inside pressure of the reaction system at 0.3 to 0.5 MPa·G. Supply of TFE was stopped when the amount of TFE reached 1.1 equivalents (11 g=110 mmol) to Nα-(t-butoxycarbonyl)tryptophan methyl ester, and stirring was continued at 120° C. Eight hours after starting of the stirring, the inside of the reaction system was brought to room temperature, followed by evacuation and refining of a crude reaction product as it was with a developing solvent of hexane and ethyl acetate of 4:1 by using silica gel chromatography to obtain 34.6 g of a product (yield: 82%).

According to a NMR analysis, it was confirmed that this product was Nα-(t-butoxycarbonyl)-N$^1$-(1,1,2,2-tetrafluoroethyl)tryptophan methyl ester. To this crude reaction product was added 2.84 g (20 mmol) of ethyl trifluoroacetate, and yield by a $^{19}$F-NMR analysis based on ethyl trifluoroacetate was 87%.

$^{19}$F-NMR (CD$_3$COCD$_3$): δ−102.4 (2F), −142.0 (2F) ppm
$^1$H-NMR (CD$_3$COCD$_3$): δ1.31 (9H, s), 2.80-3.80 (2H, m), 3.64 (3H, s), 6.50-7.80 (6H, m) ppm Example 14

Into a 50 ml autoclave was poured 6.81 g (100 mmol) of imidazole, and evacuation and replacement of atmosphere in the autoclave with nitrogen gas were carried out three times at room temperature. After the inside of a system was evacuated, vinylidene fluoride was introduced until the inside pressure of the system reached 0.1 MPa·G. Then the temperature of the reaction system was increased to 100° C. which was higher than the melting point of imidazole, and vinylidene floride was introduced to maintain the inside pressure of the reaction system at 0.3 to 0.5 MPa·G. Supply of vinylidene fluoride was stopped when the amount of vinylidene fluoride reached 1.1 equivalents (7.1 g=110 mmol) to imidazole, and stirring was continued at 100° C. Eight hours after starting of the stirring, the inside of the reaction system was brought to room temperature, followed by evacuation and then distillation in such a state to obtain 11.9 g of distillate at 99° C. (yield: 90%).

According to a NMR analysis, it was confirmed that this product was 1-(1,1-difluoroethyl)imidazole. To this crude reaction product was added 2.84 g (20 mmol) of ethyl trifluoroacetate, and yield by a $^{19}$F-NMR analysis based on ethyl trifluoroacetate was 94%.

$^{19}$F-NMR (CD$_3$COCD$_3$): δ−93.2 (2F) ppm
$^1$H-NMR (CD$_3$COCD$_3$): δ1.96 (3H, t), 7.15 (1H, s), 7.46 (1H, s), 8.01 (1H, s) ppm Example 15

Into a 50 ml autoclave was poured 6.81 g (100 mmol) of imidazole, and evacuation and replacement of atmosphere in the autoclave with nitrogen gas were carried out three times at room temperature. After the inside of a system was replaced by nitrogen gas atmosphere, the inside temperature of the autoclave was raised to 100° C. and 33.0 g (110 mmol) of perfluoro-2-methyl-2-pentene was introduced over one hour under pressurized nitrogen gas atmosphere. After stirring at 100° C. for eight hours, the inside of the reaction system was brought to room temperature, followed by evacuation and then distillation in such a state to obtain 24.7 g of distillate at 76° C./4.0 mmHg (yield: 67%).

According to a NMR analysis, it was confirmed that this product was 1-(2H-perfluoro-1-ethyl-2-methylpropyl)imidazole. To this crude reaction product was added 2.84 g (20 mmol) of ethyl trifluoroacetate, and yield by a $^{19}$F-NMR analysis based on ethyl trifluoroacetate was 75%.

$^{19}$F-NMR (CD$_3$COCD$_3$): δ−72.9 (3F), −71.8 (3F), −78.9 (3F), −121.7 (2F), −139.7 (1F, m) ppm
$^1$H-NMR (CD$_3$COCD$_3$): δ3.86 (1H, m), 7.15 (1H, s), 7.46 (1H, s), 8.01 (1H, s) ppm Example 16

Into a 50 ml autoclave was poured 6.81 g (100 mmol) of imidazole, and evacuation and replacement of atmosphere in the autoclave with nitrogen gas were carried out three times at room temperature. After the inside of a system was evacuated, perfluoro(methyl vinyl ether) (PMVE) was introduced until the inside pressure of the system reached 0.1 MPa·G. Then the temperature of the reaction system was increased to 100° C. which was higher than the melting point of imidazole, and PMVE was further introduced to maintain the inside pressure of the reaction system at 0.3 to 0.5 MPa·G. Supply of PMVE was stopped when the amount of PMVE reached 1.1 equivalents (18 g=110 mmol) to imidazole, and stirring was continued at 100° C. Eight hours after starting of the stirring, the inside of the reaction system was brought to room temperature, followed by evacuation and then distillation in such a state to obtain 18.5 g of distillate at 76° C./83 mmHg (yield: 79%).

According to a NMR analysis, it was confirmed that this product was 1-(1,1,2-trifluoro-2-trifluoromethoxyethyl)imidazole. To this crude reaction product was added 2.84 g (20 mmol) of ethyl trifluoroacetate, and yield by a $^{19}$F-NMR analysis based on ethyl trifluoroacetate was 83%.

$^{19}$F-NMR (CD$_3$COCD$_3$): δ−58.6 (3F), −93.4 (1F), −95.0 (1F), −144.0 (1F) ppm
$^1$H-NMR (CD$_3$COCD$_3$): δ7.09 (1H, dt), 7.18 (1H, s), 7.49 (1H, s), 8.04 (1H, s) ppm Example 17

Into a 50 ml three-necked flask was poured 6.81 g (100 mmol) of imidazole, and evacuation and replacement of atmosphere in the flask with nitrogen gas were carried out three times at room temperature. After the inside of a system was replaced by nitrogen gas atmosphere, 43.2 g (100 mmol) of perfluoro vinyl ether:

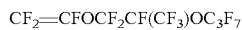

(N2VE) was added dropwise at 90° C. over one hour, and the inside temperature of the reaction system was increased to 100° C., and stirring was continued. Eight hours after starting of the stirring, the inside of the reaction system was brought to room temperature, followed by distillation in such a state to obtain 40.0 g of distillate at 90° C./2.3 mmHg (yield: 80%).

According to a NMR analysis, it was confirmed that this product was 1-(2H-perfluoro-3,6-dioxa-5-methylnonyl)imidazole:

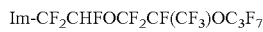

wherein Im represents an imidazole ring. To this crude reaction product was added 2.84 g (20 mmol) of ethyl trifluoroacetate, and yield by a $^{19}$F-NMR analysis based on ethyl trifluoroacetate was 81%.

$^{19}$F-NMR (CD$_3$COCD$_3$): δ−78.5−−81.5 (10F), −92.3-96.3 (2F), −128.7 (2F), −143.2−−144.0 (3F) ppm
$^1$H-NMR (CD$_3$COCD$_3$): δ7.07-7.25 (1H, m), 7.17 (1H, s), 7.44 (1H, s), 7.99 (1H, s) ppm Example 18

Into a 50 ml three-necked flask was poured 6.81 g (100 mmol) of imidazole, and evacuation and replacement of atmosphere in the flask with nitrogen gas were carried out three times at room temperature. After the inside of a system was replaced by nitrogen gas atmosphere, 34.9 g (100 mmol) of fluorinated vinyl ether:

was added dropwise at 90° C. over one hour, and the inside temperature of the reaction system was increased to 100° C., and stirring was continued. Eight hours after starting of the stirring, the inside of the reaction system was brought to room temperature, followed by distillation in such a state to obtain 32.1 g of distillate at 83° C./3.4 mmHg (yield: 77%).

According to a NMR analysis, it was confirmed that this product was 1-(2H-perfluoro-6,7-dichloro-3-oxaheptyl)imidazole:

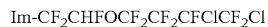

wherein Im represents an imidazole ring. To this crude reaction product was added 2.84 g (20 mmol) of ethyl trifluoroacetate, and yield by a $^{19}$F-NMR analysis based on ethyl trifluoroacetate was 80%.

$^{19}$F-NMR (CD$_3$COCD$_3$): δ−63.7 (2F), −82.2 (2F), −93.8 (1F), −95.4 (1F), −117.3 (2F), −130.8 (1F), −145.7 (1F) ppm
$^1$H-NMR (CD$_3$COCD$_3$): δ6.73 (1H, dt, J=52.8, 5.0 Hz), 7.19 (1H, s), 7.48 (1H, s), 8.04 (1H, s) ppm Example 19

Into a 50 ml three-necked flask were poured 6.83 g (100 mmol) of zinc and dioxane (20 g), followed by activation with dibromoethane under nitrogen gas atmosphere. The inside temperature of a system was increased to 100° C., and 20.9 g (50 mmol) of 1-(2H-perfluoro-6,7-dichloro-3-oxaheptyl) imidazole:

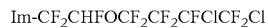

wherein Im represents an imidazole ring, was added dropwise over thirty minutes. After stirring at 100° C. for eight hours, the inside of the reaction system was brought to room temperature, followed by filtration of a reaction solution with sellaite and then distillation in such a state to obtain 12.3 g of distillate at 76° C./11 mmHg (yield: 71%).

According to a NMR analysis, it was confirmed that this product was 1-(2H-perfluoro-3-oxa-6-heptenyl)imidazole:

wherein Im represents an imidazole ring.
$^{19}$F-NMR (CD$_3$COCD$_3$): δ−80.9 (2F), −91.8 (1F), −93.1 (1F), −95.5 (1F), −107.4 (1F), −121.6 (2F), −143.5 (1F), −190.8 (1F) ppm
$^1$H-NMR (CD$_3$COCD$_3$): δ6.59 (1H, dt, J=52.2, 5.0 Hz), 7.20 (1H, s), 7.46 (1H, s), 8.02 (1H, s) ppm Example 20

Into a 50 ml three-necked flask was poured 6.81 g (100 mmol) of imidazole, and evacuation and replacement of atmosphere in the flask with nitrogen gas were carried out three times at room temperature. After the inside of a system was replaced by nitrogen gas atmosphere, 35.6 g (100 mmol) of fluorinated vinyl ether:

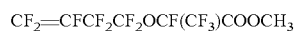

was added dropwise at 90° C. over one hour, and the inside temperature of the reaction system was increased to 100° C., and stirring was continued. Eight hours after starting of the stirring, the inside of the reaction system was brought to room temperature, followed by evacuation and refining of a crude reaction product as it was with a developing solvent of hexane and ethyl acetate of 10:1 by using silica gel chromatography to obtain 37.7 g of a product (yield: 89%).

According to a NMR analysis, it was confirmed that this was methyl product 7-(1-imidazolyl)-6H-perfluoro-2-methyl-3-oxaheptanoate:

wherein Im represents an imidazole ring. To this crude reaction product was added 2.84 g (20 mmol) of ethyl trifluoroacetate, and yield by a $^{19}$F-NMR analysis based on ethyl trifluoroacetate was 90%.

$^{19}$F-NMR (CD$_3$COCD$_3$): δ−72.8 (2F), −82.4 (3F), −87.4 (1F), −93.4 (1F), −114.3 (2F), −133.0 (1F), −207.8 (1F) ppm $^1$H-NMR (CD$_3$COCD$_3$): δ4.38 (1H, s), 6.32 (1H, m), 7.19 (1H, s), 7.52 (1H, s), 8.09 (1H, s) ppm

Example 21

Into a 100 ml three-necked flask were poured 21.2 g (50 mmol) of methyl 7-(1-imidazolyl)-6H-perfluoro-2-methyl-3-oxaheptanoate and 50 g of methanol, and thereto was added dropwise 50 ml of 1N aqueous solution of sodium hydroxide, followed by stirring at room temperature for 24 hours. Then after evacuating the inside of a system and removing the solvent, the inside temperature was elevated to 60° C., followed by 24-hour drying to obtain a solid of carboxylate.

Into a 50 ml three-necked flask equipped with a distillation column were poured the carboxylate and 20 g of tetraglyme. The inside temperature was increased to 200° C. under reduced pressure of 30 mmHg, and a produced liquid was taken out. The obtained crude reaction product was subjected to distillation as it was, and 7.61 g of distillate at 71° C./12 mmHg was obtained (yield: 44%).

According to a NMR analysis, it was confirmed that this product was 1-(2H-perfluoro-5-oxa-6-heptenyl)imidazole:

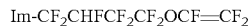

Im-CF$_2$CHFCF$_2$CF$_2$OCF=CF$_2$ wherein Im represents an imidazole ring.

$^{19}$F-NMR (CD$_3$COCD$_3$): δ−76.4 (2F), −86.2 (1F), −92.0 (1F), −112.9 (1F), −115.6 (2F), −121.2 (1F), −135.8 (1F), −210.8 (1F) ppm $^1$H-NMR (CD$_3$COCD$_3$): δ6.25 (1H, m), 7.19 (1H, s), 7.52 (1H, s), 8.03 (1H, s) ppm

Example 22

Into a 50 ml three-necked flask was poured 6.81 g (100 mmol) of imidazole, and evacuation and replacement of atmosphere in the flask with nitrogen gas were carried out three times at room temperature. After the inside of a system was replaced by nitrogen gas atmosphere, 35.8 g (100 mmol) of fluorinated vinyl ether:

CF$_2$=CFOCF$_2$CF(CF$_3$)OCF$_2$CF=CH$_2$ was added dropwise at 90° C. over one hour, and the inside temperature of the reaction system was increased to 100° C., and stirring was continued. Eight hours after starting of the stirring, the inside of the reaction system was brought to room temperature, followed by distillation in such a state to obtain 33.2 g of distillate at 90° C./2.6 mmHg (yield: 78%).

According to a NMR analysis, it was confirmed that this product was 1-(2H,9H,9H-perfluoro-3,6-dioxa-5-methyl-8-nonenyl)imidazole:

Im-CF$_2$CHFOCF$_2$CF(CF$_3$)OCF$_2$CF=CH$_2$ wherein Im represents an imidazole ring. To this crude reaction product was added 2.84 g (20 mmol) of ethyl trifluoroacetate, and yield by a $^{19}$F-NMR analysis based on ethyl trifluoroacetate was 81%.

$^{19}$F-NMR (CD$_3$COCD$_3$): δ−72.2 (2F), −78.3 (3F), −82.4−−84.2 (2F), −92.0−−94.5 (2F), −123.5 (1F), −143.2 (1F), −144.4 (1F) ppm $^1$H-NMR (CD$_3$COCD$_3$): δ5.34-5.59 (2H, m), 7.05-7.20 (1H, m), 7.16 (1H, s), 7.43 (1H, s), 8.00 (1H, s) ppm

Example 23

Into a 50 ml autoclave was poured 6.81 g (100 mmol) of imidazole, and evacuation and replacement of atmosphere in the autoclave with nitrogen gas were carried out three times at room temperature. After the inside of a system was replaced by nitrogen gas atmosphere, the inside temperature was elevated to 100° C., and 12.5 g (45 mmol) of perfluorobutenyl vinyl ether:

CF$_2$=CFOCF$_2$CF$_2$CF=CF$_2$ was introduced over one hour under pressurized nitrogen gas atmosphere, and after stirring at 100° C. for eight hours, the inside of the reaction system was brought to room temperature, followed by refining of a crude reaction product as it was with a developing solvent of hexane and ethyl acetate of 6:1 by using silica gel chromatography to obtain 14.0 g of a product (yield based on perfluorobutenyl vinyl ether: 75%).

According to a NMR analysis, it was confirmed that this product was 2-(1-imidazolyl)-1,2,2-trifluoroethyl=4-(1-imidazolyl)-1,1,2,2,3,4,4-heptafluorobutyl=ether:

Im-CF$_2$CHFOCF$_2$CF$_2$CHFCF$_2$-Im wherein Im represents an imidazole ring. To this crude reaction product was added 2.84 g (20 mmol) of ethyl trifluoroacetate, and yield by a $^{19}$F-NMR analysis based on ethyl trifluoroacetate was 78%.

$^{19}$F-NMR (CD$_3$COCD$_3$): δ−82.2 (2F), −86.4 (1F), −90.4 (1F), −92.5 (1F), −96.4 (1F), −118 (2F), −138.0 (1F), −203.9 (1F) ppm $^1$H-NMR (CD$_3$COCD$_3$): δ6.05-6.26 (1H, m), 6.98-7.09 (1H, m), 7.18 (1H, s), 7.50 (1H, s), 8.06 (1H, s) ppm

Example 24

Into a 100 ml three-necked flask was poured 6.81 g (100 mmol) of imidazole, and evacuation and replacement of atmosphere in the flask with nitrogen gas were carried out three times at room temperature. After the inside of a system was replaced by nitrogen gas atmosphere, the inside temperature was elevated to 90° C., and a solution prepared by adding 50 ml of diglyme to 59.0 g (100 mmol) of tetrafluoroethylene oligomer:

CF$_2$=CH—(CF$_2$)$_8$—I was added dropwise over one hour. After the addition, the temperature of the reaction system was elevated to 100° C. and stirring was continued. Eight hours after starting of the stirring, the inside of the reaction system was brought to room temperature. The crude reaction product was subjected to refining as it was with a developing solvent of hexane and ethyl acetate of 8:1 by using silica gel chromatography to obtain 56.1 g of a product (yield: 85%).

According to a NMR analysis, it was confirmed that this product was 1-(2H,2H-perfluoro-10-iododecyl)imidazole:

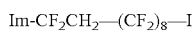

Im-CF$_2$CH$_2$—(CF$_2$)$_8$—I wherein Im represents an imidazole ring. To this crude reaction product was added 2.84 g (20 mmol) of ethyl trifluoroacetate, and yield by a $^{19}$F-NMR analysis based on ethyl trifluoroacetate was 79%.

$^{19}$F-NMR (CD$_3$COCD$_3$): δ−54.6 (2F), −94.2 (2F), −114.5 (2F), −122.0 (2F), −122.3 (4F), −123.2 (2F), −124.2 (2F), −126.7 (2F) ppm $^1$H-NMR (CD$_3$COCD$_3$): δ4.32 (2H, m), 7.20 (1H, s), 7.46 (1H, s), 8.02 (1H, s) ppm

Example 25

Into a 100 ml three-necked flask was poured 7.49 g (110 mmol) of imidazole, and evacuation and replacement of atmosphere in the flask with nitrogen gas were carried out three times at room temperature. After the inside of a system was replaced by nitrogen gas atmosphere, the inside temperature was elevated to 90° C., and a solution prepared by adding 50 ml of diglyme to 31.3 g (50 mmol) of tetrafluoroethylene oligomer:

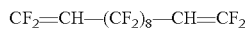

$$CF_2{=}CH{-}(CF_2)_8{-}CH{=}CF_2$$

was added dropwise over one hour. After the addition, the temperature of the reaction system was elevated to 100° C. and stirring was continued. Eight hours after starting of the stirring, the inside of the reaction system was brought to room temperature. The crude reaction product was subjected to refining as it was with a developing solvent of hexane and ethyl acetate of 3:1 by using silica gel chromatography to obtain 23.6 g of a product (yield based on a diene compound: 71%).

According to a NMR analysis, it was confirmed that this product was 1,12-bis(1-imidazolyl)-2H,2H,11H,11H-perfluorododecane:

$$Im{-}CF_2CH_2{-}(CF_2)_8{-}CH_2CF_2{-}Im$$

wherein Im represents an imidazole ring. To this crude reaction product was added 2.84 g (20 mmol) of ethyl trifluoroacetate, and yield by a $^{19}$F-NMR analysis based on ethyl trifluoroacetate was 68%.

$^{19}$F-NMR (CD$_3$COCD$_3$): δ−92.9 (4F), −119.4 (4F), −122.7 (4F), −123.7 (4F), −124.2 (4F) ppm $^1$H-NMR (CD$_3$COCD$_3$): δ4.28 (4H, m), 7.22 (2H, s), 7.46 (2H, s), 8.01 (2H, s) ppm

Example 26

Into a 100 ml three-necked flask were poured 1.36 g (20 mmol) of imidazole and 25 ml of diglyme, and evacuation and replacement of atmosphere in the flask with nitrogen gas were carried out three times at room temperature. After the inside of a system was replaced by nitrogen gas atmosphere, the inside temperature was elevated to 60° C., and a solution prepared by adding 25 ml of diglyme to 15.0 g of vinylidene fluoride polymer:

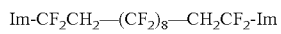

$$CF_2{=}CH{-}(CF_2CH_2)_{21.4}{-}CF_3$$

(Mn=1,500, —CH=CF$_2$ end: 63% by mole) was added dropwise over one hour. After the addition, stirring of the reaction system was continued at the temperature of 60° C. Eight hours after starting of the stirring, the inside of the reaction system was brought to room temperature. The reaction solution was poured into hexane and a precipitated product was filtrated and subjected to vacuum drying at 60° C. to obtain 13.6 g of a polymer.

According to a NMR analysis, it was confirmed that —CH=CF$_2$ end ($^{19}$F-NMR: δ−72--73 ppm (—CH=CF$_2$), $^1$H-NMR: δ4.7 ppm (—CH=CF$_2$)) had been completely consumed and this polymer was a vinylidene fluoride polymer having an imidazolyl group:

$$Im{-}CF_2CH_2{-}(CF_2CH_2)_{21.4}{-}CF_3 \ (Mn{=}1{,}540)$$

wherein Im represents an imidazole ring.

$^{19}$F-NMR (CD$_3$COCD$_3$): δ−60.4, —90--115, −95.9 ppm $^1$H-NMR (CD$_3$COCD$_3$): δ2.70-4.00, 7.20, 7.45, 8.00 ppm

Example 27

Into a 100 ml three-necked flask were poured 2.72 g (40 mmol) of imidazole and 25 ml of diglyme, and evacuation and replacement of atmosphere in the flask with nitrogen gas were carried out three times at room temperature. After the inside of a system was replaced by nitrogen gas atmosphere, the inside temperature was elevated to 60° C., and a solution prepared by adding 25 ml of diglyme to 17.0 g of vinylidene fluoride/hexafluoropropylene/tetrafluoroethylene copolymer:

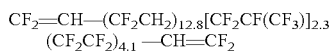

$$CF_2{=}CH{-}(CF_2CH_2)_{12.8}[CF_2CF(CF_3)]_{2.3}(CF_2CF_2)_{4.1}{-}CH{=}CF_2$$

(Mn=1,700, —CH=CF$_2$ end: 79% by mole) was added dropwise over one hour. After the addition, stirring was continued at the temperature of the reaction system of 60° C. Eight hours after starting of the stirring, the inside of the reaction system was brought to room temperature. The reaction solution was poured into hexane and a precipitated product was filtrated and subjected to vacuum drying at 60° C. to obtain 16.3 g of a polymer.

According to a NMR analysis, it was confirmed that —CH=CF$_2$ end ($^{19}$F-NMR: δ−72--73 ppm (—CH=CF$_2$), $^1$H-NMR: 4.7 ppm (—CH=CF$_2$)) had been completely consumed and this polymer was a vinylidene fluoride/hexafluoropropylene/tetrafluoroethylene copolymer having an imidazolyl group:

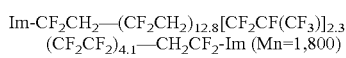

$$Im{-}CF_2CH_2{-}(CF_2CH_2)_{12.8}[CF_2CF(CF_3)]_{2.3}(CF_2CF_2)_{4.1}{-}CH_2CF_2{-}Im \ (Mn{=}1{,}800)$$

wherein Im represents an imidazole ring.

$^{19}$F-NMR (CD$_3$COCD$_3$): δ−70.2, −90.0--95.0, −96.2, −108.0--115.0, −120.0--123.0, −182.0 ppm $^1$H-NMR (CD$_3$COCD$_3$): δ2.70-4.00, 7.20, 7.45, 8.00 ppm

Example 28

Into a 30 ml three-necked flask was poured 5.00 g (29.7 mmol) of 1-(1,1,2,2-tetrafluoroethyl)imidazole synthesized in Example 1, and thereto was added dropwise 1.10 equivalents (5.36 g=32.7 mmol) of methyl trifluoromethanesulfonate (Me-OTf) at a temperature not exceeding 30° C. on ice bath under nitrogen gas atmosphere. After the addition, stirring was continued in such a state for one hour, and then a 6-hour reaction was continued at room temperature. Thereafter the inside of the system was evacuated and the inside temperature was elevated to 100° C., followed by 6-hour drying to obtain 9.31 g of a product (yield: 94%).

According to a NMR analysis, it was confirmed that this product was 1-methyl-3-(1,1,2,2-tetrafluoroethyl)imidazolium trifluoromethanesulfonate. The obtained product was a solid at room temperature.

$^{19}$F-NMR (CD$_3$COCD$_3$): δ−77.6 (3F), −98.7 (2F), −136.4 (2F) ppm $^1$H-NMR (CD$_3$COCD$_3$): δ4.21 (3H, s), 7.06 (1H, tt), 8.09 (1H, s), 8.19 (1H, s), 9.83 (1H, s) ppm

Example 29

8.49 g of 1-(1,1,2,3,3,3-hexafluoropropyl)-3-methylimidazolium trifluoromethanesulfonate was prepared (yield: 97%) in the same manner as in Example 28 except that 5.00 g (22.9 mmol) of 1-(1,1,2,3,3,3-hexafluoropropyl)imidazole synthesized in Example 4 was used instead of 1-(1,1,2,2-tetrafluoroethyl)imidazole. The obtained product was a solid at room temperature.

$^{19}$F-NMR (CD$_3$COCD$_3$): δ−73.4 (3F), −74.5 (3F), −87.7 (1F), −93.5 (1F), −210.0 (1F) ppm $^1$H-NMR (CD$_3$COCD$_3$): δ4.24 (3H, s), 6.52 (1H, m), 8.09 (1H, s), 8.26 (1H, s), 9.82 (1H, s) ppm

Example 30

8.31 g of 1-methyl-3-(1,1,2-trifluoro-2-trifluoromethoxy-ethyl)imidazolium trifluoromethanesulfonate was prepared (yield: 98%) in the same manner as in Example 28 except that 5.00 g (21.4 mmol) of 1-(1,1,2-trifluoro-2-trifluoromethoxy-ethyl)imidazole synthesized in Example 16 was used instead of 1-(1,1,2,2-tetrafluoroethyl)imidazole. The obtained product was a solid at room temperature.

$^{19}$F-NMR (CD$_3$COCD$_3$): δ−58.5 (3F), −77.1 (3F), −95.9 (1F), −97.8 (1F), −144.1 (1F) ppm $^1$H-NMR (CD$_3$COCD$_3$): δ4.21 (3H, s), 7.30 (1H, d), 8.08 (1H, s), 8.20 (1H, s), 9.77 (1H, s) ppm

Example 31

6.38 g of 1-methyl-3-(2H-perfluoro-3,6-dioxa-5-methyl-nonyl)imidazolium trifluoromethanesulfonate was prepared (yield: 96%) in the same manner as in Example 28 except that 5.00 g (10.0 mmol) of 1-(2H-perfluoro-3,6-dioxa-5-methyl-nonyl)imidazole synthesized in Example 17 was used instead of 1-(1,1,2,2-tetrafluoroethyl)imidazole. The obtained product was a highly viscous liquid at room temperature.

$^{19}$F-NMR (CD$_3$COCD$_3$): δ−78.5--81.5 (13F), −92.3--96.3 (2F), −128.0 (2F), −143.2--144.0 (3F) ppm $^1$H-NMR (CD$_3$COCD$_3$): δ7.48 (1H, dd), 8.11 (1H, s), 8.18 (1H, s), 9.82 (1H, s) ppm

Example 32

6.83 g of 1-methyl-3-(2H-perfluoro-6,7-dichloro-3-oxa-heptyl)imidazolium trifluoromethanesulfonate was prepared (yield: 98%) in the same manner as in Example 28 except that 5.00 g (12.0 mmol) of 1-(2H-perfluoro-6,7-dichloro-3-oxa-heptyl)imidazole synthesized in Example 18 was used instead of 1-(1,1,2,2-tetrafluoroethyl)imidazole. The obtained product was a solid at room temperature.

$^{19}$F-NMR (CD$_3$COCD$_3$): δ−73.4 (3F), −62.3 (2F), −80.0 (2F) −92.2 (1F), −94.6 (1F), −115.9 (2F), −128.7 (1F), −145.3 (1F) ppm $^1$H-NMR (CD$_3$COCD$_3$): δ4.21 (3H, s), 7.01 (1H, dt), 7.19 (1H, s), 7.48 (1H, s), 8.04 (1H, s), 8.10 (1H, s), 8.21 (1H, s), 9.80 (1H, s) ppm

Example 33

6.84 g of 1-methyl-3-(2H-perfluoro-3-oxa-6-heptenyl)imidazolium trifluoromethanesulfonate was prepared (yield: 93%) in the same manner as in Example 28 except that 5.00 g (14.4 mmol) of 1-(2H-perfluoro-3-oxa-6-heptenyl)imidazole synthesized in Example 19 was used instead of 1-(1,1,2,2-tetrafluoroethyl)imidazole. The obtained product was a solid at room temperature.

$^{19}$F-NMR (CD$_3$COCD$_3$): δ−76.1 (3F), −79.4 (2F), −90.2 (1F), −92.3 (1F), −94.2 (1F), −106.9 (1F), −120.2 (2F), −143.3 (1F), −190.7 (1F) ppm $^1$H-NMR (CD$_3$COCD$_3$): δ4.18 (3H, s), 6.36 (1H, dt), 8.10 (1H, s), 8.21 (1H, s), 9.80 (1H, s) ppm

Example 34

6.89 g of 1-methyl-3-(2H-perfluoro-5-oxa-6-heptenyl)imidazolium trifluoromethanesulfonate was prepared (yield: 94%) in the same manner as in Example 28 except that 5.00 g (14.4 mmol) of 1-(2H-perfluoro-5-oxa-6-heptenyl)imidazole synthesized in Example 21 was used instead of 1-(1,1,2,2-tetrafluoroethyl)imidazole. The obtained product was a solid at room temperature.

$^{19}$F-NMR (CD$_3$COCD$_3$): δ−74.5 (3F), −77.8 (2F), −83.7 (1F), −90.9 (1F), −111.2 (1F), −115.0 (2F), −120.9 (1F), −135.7 (1F), −211.2 (1F) ppm $^1$H-NMR (CD$_3$COCD$_3$): δ4.20 (3H, s), 6.41 (1H, m), 8.08 (1H, s), 8.19 (1H, s), 9.71 (1H, s) ppm

Example 35

6.56 g of 1-methyl-3-(2H,9H,9H-perfluoro-3,6-dioxa-5-methyl-8-nonenyl)imidazolium trifluoromethanesulfonate was prepared (yield: 95%) in the same manner as in Example 28 except that 5.00 g (11.7 mmol) of 1-(2H,9H,9H-perfluoro-3,6-dioxa-5-methyl-8-nonenyl)imidazole: Im-CF$_2$CHFOCF$_2$CF(CF$_3$)OCF$_2$CF=CH$_2$ synthesized in Example 22 was used instead of 1-(1,1,2,2-tetrafluoroethyl)imidazole. The obtained product was a highly viscous liquid at room temperature.

$^{19}$F-NMR (CD$_3$COCD$_3$): δ−72.2 (2F), −77.5 (3F), −78.8 (3F), −82.9 (2F), −95.2 (1F), −99.1 (1F), −123.7 (1F), −143.3 (1F), −144.3 (1F) ppm $^1$H-NMR (CD$_3$COCD$_3$): δ4.21 (3H, s), 5.42-5.61 (2H, m), 7.36-7.58 (1H, m), 8.12 (1H, s), 8.17 (1H, s), 9.83 (1H, s) ppm

Example 36

5.35 g of 1-methyl-3-(2H,2H-perfluoro-10-iododecyl)imidazolium trifluoromethanesulfonate was prepared (yield: 86%) in the same manner as in Example 28 except that 5.00 g (7.60 mmol) of 1-(2H,2H-perfluoro-10-iododecyl)imidazole synthesized in Example 24 was used instead of 1-(1,1,2,2-tetrafluoroethyl)imidazole and THF was used as a solvent. The obtained product was a solid at room temperature.

$^{19}$F-NMR (CD$_3$COCD$_3$): δ−54.8 (2F), −74.1 (3F), −94.3 (2F), −114.4 (2F), −121.9 (2F), −122.3 (4F), −123.2 (2F), −123.9 (2F), −126.8 (2F) ppm $^1$H-NMR (CD$_3$COCD$_3$): δ4.21 (3H, s), 4.48 (2H, m), 8.10 (1H, s), 8.22 (1H, s), 9.79 (1H, s) ppm

Example 37

Preparation was carried out in the same manner as in Example 28 except that 5.00 g (7.55 mmol) of 1,12-bis(1-imidazolyl)-2H,2H,11H,11H-perfluorododecane synthesized in Example 25 was used instead of 1-(1,1,2,2-tetrafluoroethyl)imidazole, THF was used as a solvent, and 2.2 equivalents of methyl trifluoromethanesulfonate was used. Thus 6.89 g of a compound, in which the first position and the twelfth position of 2H,2H, 11H, 11H-perfluorotetradecane were 1-methylimidazolium trifluoromethanesulfonate, was prepared (yield: 92%). The obtained product was a solid at room temperature.

$^{19}$F-NMR (CD$_3$COCD$_3$): δ−74.8 (6F), −90.8 (4F), −119.3 (4F), −122.5 (4F), −123.7 (4F), −124.3 (4F) ppm $^1$H-NMR (CD$_3$COCD$_3$): δ4.20 (6H, s), 4.53 (4H, m), 8.11 (2H, s), 8.27 (2H, s), 9.77 (2H, s) ppm

Example 38

5.20 g of a vinylidene fluoride polymer (Mn=1,630) comprising 1-methylimidazolium trifluoromethanesulfonate was prepared in the same manner as in Example 28 except that 5.00 g of vinylidene fluoride polymer (Mn=1,540) having 63% by mole of imidazolyl group at its end and synthesized in Example 26 was used instead of 1-(1,1,2,2-tetrafluoroethyl)

imidazole, and THF was used as a solvent. The obtained product was a solid at room temperature.

$^{19}$F-NMR (CD$_3$COCD$_3$): δ−60.6, −75.3, −89.0-−115.0, −98.9 ppm $^{1}$H-NMR (CD$_3$COCD$_3$): δ2.70-4.00, 4.20, 4.81, 8.08, 8.26, 9.82 ppm Example 39

5.63 g of a vinylidene fluoride/hexafluoropropylene/tetrafluoroethylene copolymer (Mn=2,050) comprising 1-methylimidazolium trifluoromethanesulfonate at both ends thereof was prepared in the same manner as in Example 28 except that 5.00 g of the vinylidene fluoride/hexafluoropropylene/tetrafluoroethylene copolymer (Mn=1,800) having 79% by mole of imidazolyl group at its end and synthesized in Example 27 was used instead of 1-(1,1,2,2-tetrafluoroethyl)imidazole, and THF was used as a solvent. The obtained product was a solid at room temperature.

$^{19}$F-NMR (CD$_3$COCD$_3$): δ−70.3, −73.8, −90-−95, −96, −108.0-−115.0, −120-−123, −182.0 ppm $^{1}$H-NMR (CD$_3$COCD$_3$): δ2.70-4.00, 4.20, 4.79, 8.10, 8.25, 9.77 ppm Example 40

Into a 50 ml three-necked autoclave were poured 10.0 g (59.4 mmol) of 1-(1,1,2,2-tetrafluoroethyl)imidazole prepared in Example 1 and 20 ml of dichloromethane, and evacuation and replacement of atmosphere in the autoclave with nitrogen gas were carried out three times on dry ice/acetone bath. After the inside of the system was evacuated, 8.46 g (89.2 mmol) of methyl bromide was added thereto. After the addition, a 6-hour reaction was carried out at 60° C. Thereafter the inside of the system was evacuated and the inside temperature was elevated to 100° C., followed by 6-hour drying to obtain 13.7 g of a product (yield: 88%). The obtained product was a solid at room temperature.

According to a NMR analysis, it was confirmed that this product was 1-methyl-3-(1,1,2,2-tetrafluoroethyl)imidazolium bromide.

$^{19}$F-NMR (CD$_3$COCD$_3$): δ−96.5 (2F), −134.1 (2F) ppm $^{1}$H-NMR (CD$_3$COCD$_3$): δ4.17 (3H, s), 7.04 (1H, tt), 8.10 (1H, s), 8.21 (1H, s), 9.80 (1H, s) ppm Example 41

Into a 50 ml three-necked autoclave were poured 10.0 g (45.9 mmol) of 1-(1,1,2,3,3,3-hexafluoropropyl)imidazole prepared in Example 4 and 20 ml of dichloromethane, and evacuation and replacement of atmosphere in the autoclave with nitrogen gas were carried out three times on dry ice/acetone bath. After the inside of the system was evacuated, 6.53 g (68.8 mmol) of methyl bromide was added thereto. After the addition, a 6-hour reaction was carried out at 60° C. Thereafter the inside of the system was evacuated and the inside temperature was elevated to 100° C., followed by 6-hour drying to obtain 12.9 g of a product (yield: 90%). The obtained product was a solid at room temperature.

According to a NMR analysis, it was confirmed that this product was 1-(1,1,2,3,3,3-hexafluoropropyl)-3-methylimidazolium bromide.

$^{19}$F-NMR (CD$_3$COCD$_3$): δ−75.1 (3F), −88.9 (1F), −92.0 (1F), −210.3 (1F) ppm $^{1}$H-NMR (CD$_3$COCD$_3$): δ6.51 (1H, m), 8.12 (1H, s), 8.27 (1H, s), 9.91 (1H, s) ppm Example 42

Into a 50 ml two-necked flask were poured 2.50 g (9.50 mmol) of 1-methyl-3-(1,1,2,2-tetrafluoroethyl)imidazolium bromide synthesized in Example 40 and 20 ml of dichloromethane, and thereto was added dropwise a solution prepared by dissolving 6.60 g (9.50 mmol) of silver carboxylate containing perfluoro polyether:

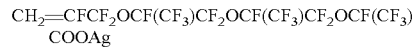
COOAg in 20 ml of dichloromethane. After the addition, stirring was continued for one hour in such a state, and then the reaction solution was filtrated with sellaite and the temperature was elevated to 80° C. under reduced pressure, followed by 6-hour drying to obtain 7.17 g of a product (yield: 98%). The obtained product was a highly viscous liquid at room temperature.

According to a NMR analysis, it was confirmed that this product was 1-methyl-3-(1,1,2,2-tetrafluoroethyl)imidazolium 12H, 12H-perfluoro-2,5,8-trimethyl-3,6,9-trioxa-11-dodecenoate.

$^{19}$F-NMR (CD$_3$COCD$_3$): δ−72.6 (2F), 87.5-85.0 (13F), −96.5 (2F), −113.6 (1F), −123.2 (1F), −133.5 (2F), −144.3 (2F) ppm $^{1}$H-NMR (CD$_3$COCD$_3$): δ4.21 (3H, s), 5.42-5.62 (2H, m), 7.10 (1H, tt), 8.10 (1H, s), 8.19 (1H, s), 10.00 (1H, s) ppm Example 43

5.88 g of 1-methyl-3-(1,1,2,2-tetrafluoroethyl)imidazolium perfluoro-3,6-dioxa-4-methyl-7-octenesulfonate was prepared (yield: 99%) in the same manner as in Example 42 by using 2.50 g (9.50 mmol) of 1-methyl-3-(1,1,2,2-tetrafluoroethyl)imidazolium bromide and 20 ml of dichloromethane except that 5.23 g (9.50 mmol) of silver sulfonate containing perfluoro polyether:

was used. The obtained product was a highly viscous liquid at room temperature.

$^{19}$F-NMR (CD$_3$COCD$_3$): δ−80.0-−87.0 (7F), −95.5 (2F), −113.3 (2F), −114.2 (1F), −122.8 (1F), −133.9 (2F), −136.8 (1F), −146.0 (1F) ppm $^{1}$H-NMR (CD$_3$COCD$_3$): δ4.18 (3H, s), 7.11 (1H, tt), 8.10 (1H, s), 8.20 (1H, s), 9.91 (1H, s) ppm Example 44

Into a 50 ml two-necked flask were poured 1.71 g of poly (sodium methacrylate):

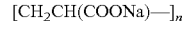

(weight average molecular weight: 6,500) and 20 ml of water, and thereto was added dropwise 5.00 g (19.0 mmol) of 1-methyl-3-(1,1,2,2-tetrafluoroethyl)imidazolium bromide. After the addition, a polymer was precipitated. The precipitated polymer was washed with water, followed by 8-hour vacuum drying at 60° C. to obtain 5.02 g of a polymer.

According to a NMR analysis, it was confirmed that this polymer was poly[1-methyl-3-(1,1,2,2-tetrafluoroethyl)imidazolium methacrylate] having a polymer side chain converted to imidazolium cation.

$^{19}$F-NMR (CD$_3$COCD$_3$): δ−94.8 (2F), −134.7 (2F) ppm $^{1}$H-NMR (CD$_3$COCD$_3$): δ1.30-1.55 (3H), 1.95-2.45 (2H), 3.97 (3H), 6.95-7.00 (1H), 8.10 (1H, s), 8.20 (1H), 10.0 (1H) ppm

Example 45

Into a 50 ml two-necked flask were poured 6.18 g (10.5 mmol) of carboxylic acid containing perfluoro polyether:

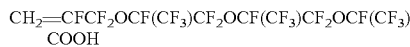
CH$_2$=CFCF$_2$OCF(CF$_3$)CF$_2$OCF(CF$_3$)CF$_2$OCF(CF$_3$)COOH and 20 ml of tetrahydrofuran, and thereto was added dropwise 1.95 g (11.6 mmol) of 1-(1,1,2,2-tetrafluoroethyl)imidazole. After the addition, one-hour stirring was carried out in such a state, and then the temperature was elevated to 80° C. under reduced pressure, followed by 6-hour drying to obtain 7.77 g of a product (yield based on carboxylic acid: 98%). The obtained product was a highly viscous liquid at room temperature.

According to a NMR analysis, it was confirmed that this product was 1-(1,1,2,2-tetrafluoroethyl)imidazolium 12H,12H-perfluoro-2,5,8-trimethyl-3,6,9-trioxa-11-dodecenoate.

$^{19}$F-NMR (CD$_3$COCD$_3$): δ−72.4 (2F), 87.5-85.0 (13F), −96.2 (2F), −113.8 (1F), −122.9 (1F), −133.2 (2F), −143.6 (2F) ppm $^{1}$H-NMR (CD$_3$COCD$_3$): δ1.60 (1H), 5.42-5.62 (2H, m), 6.99 (1H, m), 8.10 (1H, s), 8.20 (1H, s), 9.82 (1H, s) ppm

Example 46

6.31 g of 1-(1,1,2,2-tetrafluoroethyl)imidazolium perfluoro-3,6-dioxa-4-methyl-7-octenesulfonate was prepared (yield: 98%) in the same manner as in Example 44 by using 4.66 g (10.5 mmol) of sulfonic acid containing perfluoro polyether:

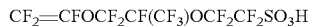
CF$_2$=CFOCF$_2$CF(CF$_3$)OCF$_2$CF$_2$SO$_3$H and 1.95 g (11.6 mmol) of 1-(1,1,2,2-tetrafluoroethyl)imidazole. The obtained product was a highly viscous liquid at room temperature.

$^{19}$F-NMR (CD$_3$COCD$_3$): δ−80.0--87.0 (7F), −94.9 (2F), −113.0 (2F), −113.9 (1F), −122.9 (1F), −133.6 (2F), −137.2 (1F), −145.0 (1F) ppm $^{1}$H-NMR (CD$_3$COCD$_3$): δ1.60 (1H), 7.07 (1H, tt), 8.08 (1H, s), 8.21 (1H, s), 9.79 (1H, s) ppm

Example 47

7.61 g of a polymer was prepared in the same manner as in Example 44 except that 20 ml of acetone was used as a solvent instead of water, and 3.87 g of poly(4-styrenesulfonic acid):

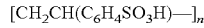
[CH$_2$CH(C$_6$H$_4$SO$_3$H)—]$_n$ (MW: 70,000) and 3.90 g (23.2 mmol) of 1-(1,1,2,2-tetrafluoroethyl)imidazole were used.

According to a NMR analysis, it was confirmed that the obtained product was poly[1-(1,1,2,2-tetrafluoroethyl)imidazolium 4-styrenesulfonate] having a polymer side chain converted to imidazolium cation (yield: 98%).

$^{19}$F-NMR (CD$_3$COCD$_3$): δ−94.8 (2F), −134.7 (2F) ppm $^{1}$H-NMR (CD$_3$COCD$_3$): δ1.40-1.60 (2H), 1.80-2.25 (2H), 6.30-7.10 (5H), 8.12 (1H, s), 8.22 (1H, s), 10.0 (1H) ppm

Example 48

Into a 50 ml two-necked flask were poured 3.19 g (10.2 mmol) of 1-(1,1,2,3,3,3-hexafluoropropyl)-3-methylimidazolium bromide and 20 ml of dichloromethane, and thereto was added dropwise a solution prepared by dissolving 2.08 g (10.7 mmol) of silver tetrafluoroborate in 20 ml of dichloromethane. After the addition, stirring was continued for one hour in such a state, and then the reaction solution was filtrated with sellaite and the temperature was elevated to 100° C. under reduced pressure, followed by 6-hour drying to obtain 3.10 g of a product (yield: 95%). The obtained product was a highly viscous liquid at room temperature.

According to a NMR analysis, it was confirmed that this product was 1-(1,1,2,3,3,3-hexafluoropropyl)-3-methylimidazolium tetrafluoroborate subjected to anion exchange of bromine with tetrafluoroboric acid.

$^{19}$F-NMR (CD$_3$COCD$_3$): δ−77.0 (3F), −87.8 (1F), −91.2 (1F), −150.0 (4F), −209.8 (1F) ppm $^{1}$H-NMR (CD$_3$COCD$_3$): δ6.62 (1H, m), 8.09 (1H, s), 8.24 (1H, s), 9.79 (1H, s) ppm

Example 49

Preparation was carried out in the same manner as in Example 48 by using 3.19 g (10.2 mmol) of 1-(1,1,2,3,3,3-hexafluoropropyl)-3-methylimidazolium bromide and 2.70 g (10.7 mmol) of silver hexafluorophosphate. Thus 3.70 g of 1-methyl-3-(1,1,2,3,3,3-hexafluoropropyl)imidazolium hexafluorophosphate subjected to anion exchange of bromine with hexafluorophosphoric acid was prepared (yield: 96%). The obtained product was a highly viscous liquid at room temperature.

$^{19}$F-NMR (CD$_3$COCD$_3$): δ−61.6 (6F), −73.6 (3F), −86.9 (1F), −94.6 (1F), −210.3 (1F) ppm $^{1}$H-NMR (CD$_3$COCD$_3$): δ6.56 (1H, m), 8.10 (1H, s), 8.26 (1H, s), 9.88 (1H, s) ppm

Example 50

Into a 50 ml two-necked flask were poured 3.19 g (10.2 mmol) of 1-(1,1,2,3,3,3-hexafluoropropyl)-3-methylimidazolium bromide and 20 ml of water, and thereto was added dropwise 3.50 g (12.2 mmol) of lithium bis(trifluoromethanesulfonyl)imide. Then the temperature inside a system was increased to 70° C., followed by 6-hour stirring. After the inside the system was brought to room temperature, an organic layer was separated, followed by extraction with chloroform three times, drying with magnesium sulfate, removal of chloroform under reduced pressure, elevation of the inside temperature to 100° C. under reduced pressure, and then 6-hour drying. 4.70 g of a product was obtained (yield: 89%). The obtained product was a liquid at room temperature.

According to a NMR analysis, it was confirmed that this product was 1-(1,1,2,3,3,3-hexafluoropropyl)-3-methylimidazolium bis(trifluoromethanesulfonyl)imide subjected to anion exchange of bromine with bis(trifluoromethanesulfonyl)imidic acid.

$^{19}$F-NMR (CD$_3$COCD$_3$): δ−73.1 (3F), −79.0 (6F), −87.3 (1F), −93.3 (1F), −209.4 (1F) ppm $^{1}$H-NMR (CD$_3$COCD$_3$): δ4.26 (3H, s), 6.78 (1H, m), 8.09 (1H, s), 8.25 (1H, s), 9.99 (1H, s) ppm

Example 51

5.32 g of 1-(1,1,2,3,3,3-hexafluoropropyl)-3-methylimidazolium bis(pentafluoroethanesulfonyl)imide subjected to anion exchange of bromine with bis(pentafluoromethanesulfonyl)imidic acid was prepared (yield: 85%) in the same manner as in Example 50 by using 3.19 g (10.2 mmol) of 1-(1,1,2,3,3,3-hexafluoropropyl)-3-methylimidazolium bromide except that 4.93 g (12.2 mmol) of sodium bis(pentafluoroethanesulfonyl)imide was used. The obtained product was a highly viscous liquid at room temperature.

$^{19}$F-NMR (CD$_3$COCD$_3$): δ−74.2 (3F), −81.3 (6F), −87.3 (1F), −93.3 (1F), −123.1 (2F), −125.2 (2F), −209.4 (1F) ppm $^{1}$H-NMR (CD$_3$COCD$_3$): δ4.23 (3H, s), 6.79 (1H, m), 8.10 (1H, s), 8.26 (1H, s), 10.02 (1H, s) ppm

Example 52

5.40 g of 1-(1,1,2,3,3,3-hexafluoropropyl)-3-methylimidazolium tris(trifluoromethanesulfonyl)methide subjected to anion exchange of bromine with tris(trifluoromethanesulfonyl)carbon acid was prepared (yield: 82%) in the same manner as in Example 50 by using 3.19 g (10.2 mmol) of 1-(1,1,2,3,3,3-hexafluoropropyl)-3-methylimidazolium bromide except that 5.10 g (12.2 mmol) of lithium tris(trifluoromethanesulfonyl)methide was used. The obtained product was a highly viscous liquid at room temperature.

$^{19}$F-NMR (CD$_3$COCD$_3$): δ−73.0 (3F), −78.5 (9F), −87.4 (1F), −91.7 (1F), −210.2 (1F) ppm
$^1$H-NMR (CD$_3$COCD$_3$): δ4.20 (3H, s), 6.79 (1H, m), 8.09 (1H, s), 8.24 (1H, s), 9.96 (1H, s) ppm

Example 53

2.47 g of 1-(1,1,2,3,3,3-hexafluoropropyl)-3-methylimidazolium dicyanamide subjected to anion exchange of bromine with dicyanimidic acid was prepared (yield: 81%) in the same manner as in Example 50 by using 3.19 g (10.2 mmol) of 1-(1,1,2,3,3,3-hexafluoropropyl)-3-methylimidazolium bromide except that 1.09 g (12.2 mmol) of sodium dicyanamide was used. The obtained product was a solid.

$^{19}$F-NMR (CD$_3$COCD$_3$): δ−74.4 (3F), −89.2 (1F), −94.1 (1F), −209.7 (1F) ppm
$^1$H-NMR (CD$_3$COCD$_3$): δ4.19 (3H, s), 6.81 (1H, m), 8.11 (1H, s), 8.23 (1H, s), 10.02 (1H, s) ppm

Example 54

3.55 g of 1-(1,1,2,3,3,3-hexafluoropropyl)-3-methylimidazolium hexafluoroacetylacetonate subjected to anion exchange of bromine with hexafluoroacetylacetonate was prepared (yield: 79%) in the same manner as in Example 50 by using 3.19 g (10.2 mmol) of 1-(1,1,2,3,3,3-hexafluoropropyl)-3-methylimidazolium bromide except that 2.61 g (12.2 mmol) of lithium•hexafluoroacetylacetonate was used. The obtained product was a highly viscous liquid.

$^{19}$F-NMR (CD$_3$COCD$_3$): δ−73.8 (3F), −77.4 (6F), −86.8 (1F), −92.6 (1F), −209.6 (1F) ppm
$^1$H-NMR (CD$_3$COCD$_3$): δ4.23 (3H, s), 6.40 (1H, s), 6.84 (1H, m), 8.09 (1H, s), 8.24 (1H, s), 9.80 (1H, s) ppm

INDUSTRIAL APPLICABILITY

According to the preparation process of the present invention, a N—H group of a heteroaromatic ring compound can be converted directly to a N—Rf group at a high reaction yield without using a catalyst. In addition, according to this preparation process, many kinds of novel fluorine-containing compounds can be easily synthesized, and as a result, a fluorine-containing ionic liquid having a low melting point and characterized by easily compatibilizing a polar compound in a matrix such as a fluorine-containing solvent or a fluorine-containing resin can be obtained.

The invention claimed is:

1. A salt of fluorine-containing imidazole compound represented by the structural formula (E-1):

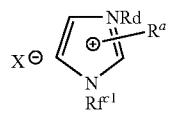

wherein $R^a$ may or may not be present and when $R^a$ is present, the whole or a part of the hydrogen atoms of the heteroaromatic ring may be substituted by an $R^a$, wherein an $R^a$ is independently a halogen atom, a functional group or an organic group; $Rf^{c1}$ is a fluoroalkyl group represented by the formula (c):

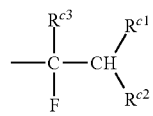

wherein $R^{c1}$, $R^{c2}$ and $R^{c3}$ are the same or different and each is H, halogen atom, a functional group or a monovalent organic group which may be substituted by halogen atom, may have an ether bond and may have a polymerizable group, or a monovalent organic group which may have at least one residue defined by deleting $R^{c1}$ group from the formula (C-1):

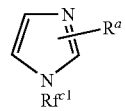

wherein $R^a$ and $R^{c1}$ are as defined above; at least one of $R^{c1}$, $R^{c2}$ and $R^{c3}$ in said formula (c) has at its end at least one polymerizable group which is a carbon-carbon double bond; Rd is H or a monovalent organic group; and X is a counter anion.

2. The salt of fluorine-containing imidazole compound of claim 1, wherein at least one of $R^{c1}$, $R^{c2}$ and $R^{c3}$ in said formula (c) comprises a moiety represented by the formula (b-1):

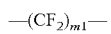

wherein m1 is an integer of 1 to 10,000,
the formula (b-2):

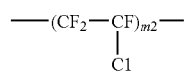

wherein m2 is an integer of 1 to 10,000,
the formula (b-3):

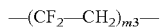

wherein m3 is an integer of 1 to 10,000
the formula (b-4):

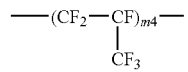

wherein m4 is an integer of 1 to 3,000, or
the formula (b-5):

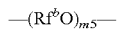

wherein $Rf^b$ is a linear or branched alkylene group having fluorine atom; m5 is an integer of 1 to 100.

* * * * *